United States Patent
Jusoh et al.

(10) Patent No.: US 10,457,759 B2
(45) Date of Patent: Oct. 29, 2019

(54) CO-DELIVERY OF CHOLESTEROL LOWERING DRUGS AND NUTRACEUTICALS

(71) Applicants: International Business Machines Corporation, Armonk, NY (US); Nanomalaysia Berhad, Kuala Lumpur (MY)

(72) Inventors: Mohd Zulkefeli Bin Mat Jusoh, Kuala Lumpur (MY); Alshakim Nelson, Montlake, WA (US); Victoria A. Piunova, Los Gatos, CA (US); Joseph Sly

(73) Assignees: International Business Machines Corporation, Armonk, NY (US); NanoMalaysia Berhad, Kuala Lumpur (MY)

(*) Notice: Subject to any disclaimer, the term of this patent is extended or adjusted under 35 U.S.C. 154(b) by 71 days.

(21) Appl. No.: 15/654,773

(22) Filed: Jul. 20, 2017

(65) Prior Publication Data
US 2019/0023824 A1   Jan. 24, 2019

(51) Int. Cl.
| | |
|---|---|
| C08F 212/08 | (2006.01) |
| C08F 212/36 | (2006.01) |
| A61K 9/00 | (2006.01) |
| A61K 47/32 | (2006.01) |
| A61K 47/34 | (2017.01) |
| A61K 9/107 | (2006.01) |
| A61K 47/42 | (2017.01) |
| C08F 297/02 | (2006.01) |
| C08F 295/00 | (2006.01) |
| A61K 9/20 | (2006.01) |

(52) U.S. Cl.
CPC ........... *C08F 212/08* (2013.01); *A61K 9/0019* (2013.01); *A61K 9/0053* (2013.01); *A61K 9/1075* (2013.01); *A61K 47/32* (2013.01); *A61K 47/34* (2013.01); *A61K 47/42* (2013.01); *C08F 212/36* (2013.01); *C08F 295/00* (2013.01); *C08F 297/02* (2013.01); *A61K 9/0031* (2013.01); *A61K 9/0095* (2013.01); *A61K 9/2063* (2013.01); *C08F 2438/01* (2013.01); *C08F 2500/24* (2013.01)

(58) Field of Classification Search
CPC .. C08F 212/08; C08F 212/36; C08F 2500/24; A61K 9/0053; C08L 53/085; C08L 53/025
See application file for complete search history.

(56) References Cited

U.S. PATENT DOCUMENTS

| | | | |
|---|---|---|---|
| 2010/0159001 A1* | 6/2010 | Cardinal et al. ..... | A61K 9/2009 424/457 |
| 2010/0160363 A1 | 6/2010 | Cardinal et al. | |
| 2011/0243848 A1* | 10/2011 | Appel et al. ........ | A61K 49/0036 424/9.1 |
| 2013/0144014 A1 | 6/2013 | Zhao | |
| 2014/0301970 A1* | 10/2014 | Hedrick et al. .... | C08G 65/3318 424/78.37 |

FOREIGN PATENT DOCUMENTS

WO    2011163635 A1    12/2011

OTHER PUBLICATIONS

Lee, et al., "Nanogel Star Polymer Architectures: A Nanoparticle Platform for Modular Programmable Macromolecular SelfAssembly, Intercellular Transport, and Dual-Mode Cargo Delivery", Advanced Materials, . 2011, 23, pp. 4509-4515.
Appel, et al., "Toward biodegradable nanogel star polymers via organocatalytic ROP", Chem. Commun., 2012, 48, pp. 6163-6165.

* cited by examiner

*Primary Examiner* — Nathan M Nutter
(74) *Attorney, Agent, or Firm* — Michael R. Roberts

(57) ABSTRACT

Star polymer occlusion complexes were prepared comprising i) an amphiphilic unimolecular star polymer having a crosslinked core covalently linked to 6 or more independent amphiphilic polymer arms, ii) a nutraceutical (such as coenzyme Q10), and iii) a cholesterol-lowering drug (such as simvastatin). An initial occlusion complex formed with the nutraceutical and the star polymer exhibited improved binding properties for the cholesterol-lowering drug, resulting in improved loading efficiencies for the cholesterol-lowering drug. The star polymer occlusion complexes have utility in the medical treatment of high blood cholesterol.

21 Claims, 3 Drawing Sheets

CO-DELIVERY OF CHOLESTEROL LOWERING DRUGS AND NUTRACEUTICALS

PARTIES TO A JOINT RESEARCH AGREEMENT

This invention was made under a joint research agreement between International Business Machines Corporation and NanoMalaysia Berhad.

BACKGROUND

The present invention relates to co-delivery of cholesterol lowering drugs with neutraceuticals, and more specifically, to co-encapsulation and co-delivery of cholesterol lowering drugs with coenzyme Q10 and related compounds using nanogel core star polymers as carriers.

A sedentary life style and a diet high in animal protein and fat promote high-cholesterol induced diseases. A common strategy to reduce elevated levels of cholesterol is statin therapy. While statins successfully lower cholesterol levels in the blood stream they also elicit undesirable side effects, such as an inhibition of ubiquinone (coenzyme Q10, also referred to herein as CoQ10) biosynthesis and consequently statin cardiomyopathy. The leading strategy to negate this side effect is to supplement the statin therapy with large doses of synthetic CoQ10. While effective, this approach is not free of drawbacks. First, poor bioavailability of CoQ10 significantly lowers the actual levels of the supplement absorbed by the body, and second, a regimen that requires administration of multiple pills several times a day is difficult for patients to adhere to.

Therefore, a need exists for more efficient delivery of both cholesterol lowering drugs and nutraceuticals (such as CoQ10) that are affected by the cholesterol lowering therapy.

SUMMARY

Accordingly, a loaded star polymer is disclosed, comprising:
 a star polymer macromolecule, the star polymer comprising a crosslinked hydrophobic core covalently linked to a plurality of block polymer arms emanating from the core, wherein each arm comprises i) a hydrophobic first block linked to the core and ii) a peripheral second block linked to the first block, the second block comprising a repeat unit containing a sidechain tertiary amine group capable of undergoing protonation to form a hydrophilic tertiary ammonium ion;
 a cholesterol lowering drug selected from the group consisting of simvastatin, lovastatin, atorvastatin, fluvastatin, pitavastatin, pravastatin, and rosuvastatin, and combinations thereof; and
 a nutraceutical selected from the group consisting of ubiquinone (coenzyme Q10), menadione, duroquinone, idebenone, decylubiquinone, and combinations thereof; wherein
 the star polymer, the cholesterol lowering drug, and the nutraceutical are bound together by non-covalent interactions, and
 the loaded star polymer is water-dispersible.

Also disclosed is a method of forming an above-described loaded star polymer, comprising:
 adding with agitation i) a first mixture comprising the nutraceutical and a first organic solvent to ii) a second mixture comprising the star polymer and a second organic solvent, thereby forming a third mixture;
 adding with agitation, to the third mixture, iii) a fourth mixture comprising the cholesterol-lowering drug and a third organic solvent, thereby forming a fifth mixture;
 adding with agitation water to the fifth mixture, thereby forming the loaded star polymer.

Further disclosed is a medical composition, comprising:
 an above-described loaded star polymer; and
 a second component in contact with the loaded star polymer.

The above-described and other features and advantages of the present invention will be appreciated and understood by those skilled in the art from the following detailed description, drawings, and appended claims.

DETAILED DESCRIPTION

Disclosed are water-dispersible nano-sized occlusion complexes comprising a nanogel star polymer macromolecule, one or more molecules of a cholesterol-lowering agent, and one or more molecules of a nutraceutical, all bound together by non-covalent interactions (e.g., hydrophobic interactions and/or ionic interactions). The occlusion complexes are also referred to herein as "loaded star polymers". The star polymer macromolecule serves as a carrier for delivery and release of the cholesterol-lowering drug and nutraceutical (also referred to herein as "cargo" materials). Methods of making the loaded star polymers are also disclosed. Further disclosed are nano-sized particles comprising one or more loaded star polymer macromolecules bound together by non-covalent interactions. The particles are capable of releasing the cholesterol-lowering drug and the nutraceutical in water at a pH of less than 7, more particularly less than 6.

The nanogel star polymer macromolecule, or simply "star polymer", comprises a hydrophobic crosslinked polymer core and six or more independent amphiphilic block polymer arms covalently linked to, and emanating from, the core. A given block polymer arm comprises i) a hydrophobic polymer block A, which is directly covalently linked to the core and ii) a peripheral hydrophilic block B, which is covalently linked to block A.

Figure 1A:
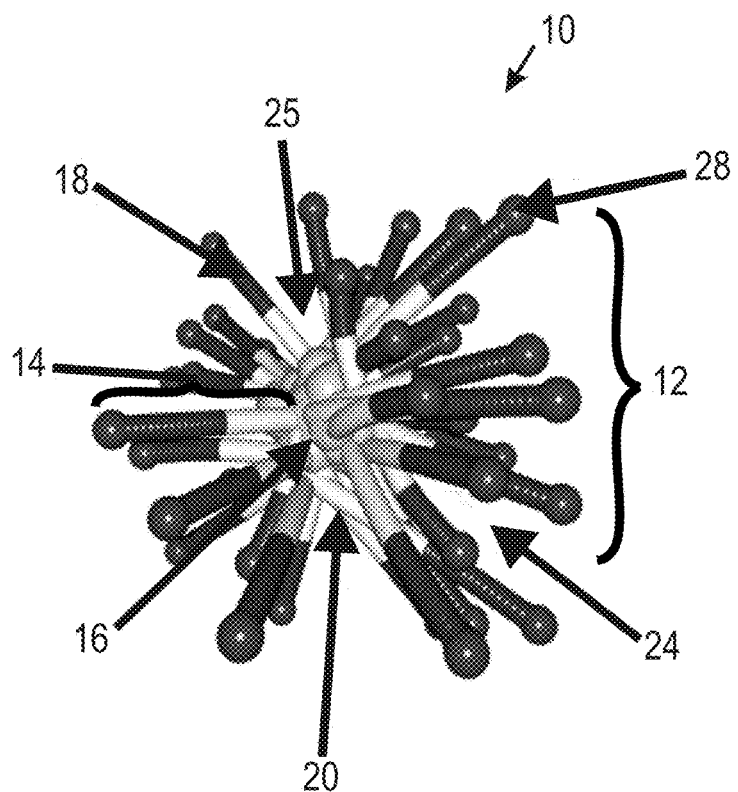
FIG. 1A is a three-dimensional drawing representation of a unimolecular star polymer.
Figure 1B:
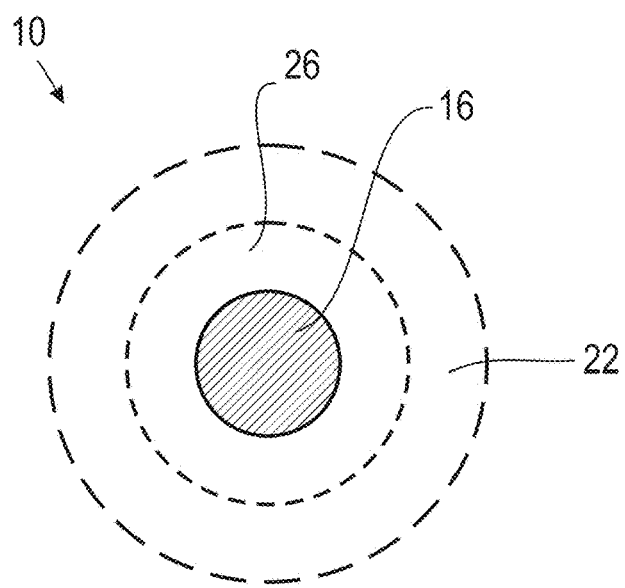
FIG. 1B is a graphical layer diagram illustrating the hydrophilic and hydrophobic sub-regions of an exemplary star polymer.

The following drawings are meant to be illustrative and non-limiting. FIG. 1A is a three-dimensional drawing representation of star polymer 10. FIG. 1B is a graphical layer diagram illustrating the hydrophilic and hydrophobic sub-regions of star polymer 10. Star polymer 10 comprises six or more independent amphiphilic block polymer arms 14. Each block polymer arm 14 is covalently linked at one end to a central crosslinked hydrophobic polymer core 16. Polymer core 16 can be a living core or a passive core (i.e., having no reactive groups to introduce additional functionality). Each block polymer arm 14 comprises an inner hydrophobic block A 20 (white tone in FIG. 1A) and a peripheral hydrophilic block B 18 (dark tone in FIG. 1A). Region 12 comprises the collection of polymer arms 14. In this example, region 12 has two sub-regions: a peripheral hydrophilic sub-region 22 (FIG. 1B) comprising the peripheral hydrophilic block B 18 and peripheral interstitial areas 24 (FIG. 1A), and an inner hydrophobic sub-region 26 (FIG. 1B) composed of the inner hydrophobic block A 20 and inner interstitial areas 25 (FIG. 1A). The dashed boundary lines around peripheral sub-region 22 and inner sub-region 26 in FIG. 1B indicate the boundary between peripheral interstitial areas 24 and inner interstitial areas 25. End group 28 of polymer arm 14 is also shown.

Polymer arms 14 are preferably linear in structure, meaning the arms are composed of one polymer branch rather than intersecting polymer branches. A given branch has a polymer backbone, defined herein as the collection of covalently linked atomic centers forming the shortest path of covalent bonds of a given arm from the end repeat unit closest to the core to the opposing end repeat unit of the given arm farthest from the core. The polymer backbone includes atomic centers of any linking group joining adjacent polymer blocks of the given arm that are part of the shortest path. The peripheral end groups 28 of polymer arms 14 are independent of one another and can be chemically active or inactive with respect to the loading properties, release properties, and/or biodegradable properties of the star polymers.

No restriction is placed on the number of polymer blocks of the polymer arms. A given polymer arm can comprise one or more hydrophilic polymer blocks and/or one or more hydrophobic polymer blocks. The peripheral sub-region 22, the inner sub-region 26, and/or the crosslinked polymer core 16 can also contain specific sites for further functionalization, which can be useful in controlling chemical interactions that favor the binding and/or release of an occluded cargo material, and/or the biodegradability of the star polymer. As a non-limiting example, the polymer core 16 can be a "living" core capable of initiating a polymerization or undergoing a different chemical modification. As another non-limiting example, the polymer arms 14 can comprise a functionally useful end group 28, such as a galactose moiety capable of selective recognition of liver cells.

Figure 1C:
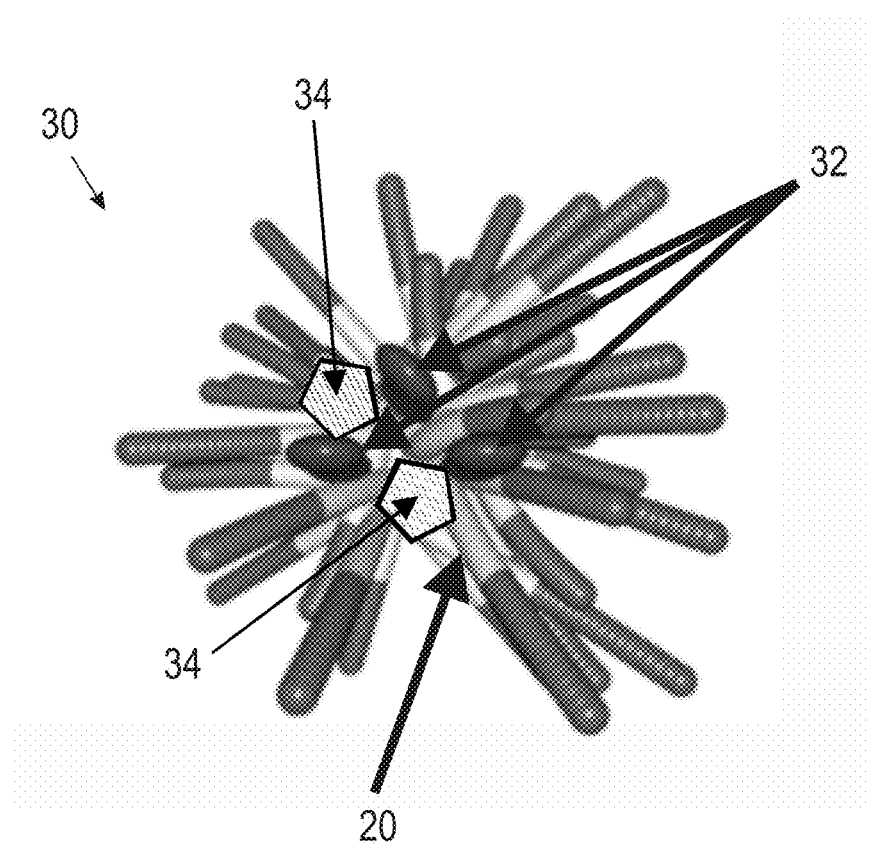
FIG. 1C is a three-dimensional drawing representation an exemplary loaded star polymer comprising two molecules of a nutraceutical and three molecules of a cholesterol-lowering drug.

FIG. 1C is a three-dimensional drawing representation of an exemplary loaded star polymer 30, comprising three cholesterol-lowering drug molecules 32 and two nutraceutical molecules 34, which are in contact with the polymer arms and/or core of star polymer 10. Although the occluded cargo materials are primarily associated with the hydrophobic regions of star polymer 10, they can also reside to some extent in contact with the peripheral hydrophilic block B 18.

The star polymer preferably has a molecular formula containing none of the following restricted metals: ionic and nonionic forms of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table. Metals of Groups 3 to 12 of the Periodic Table include scandium, titanium, vanadium, chromium, manganese, iron, cobalt, nickel, copper, zinc, yttrium, zirconium, niobium, molybdenum, technetium, ruthenium, rhodium, palladium, silver, cadmium, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, iridium, platinum, gold, mercury, actinium, thorium, protactinium, uranium, neptunium, plutonium, americium, curium, berkelium, californium, einsteinium, fermium, mendelevium, nobelium, lawrencium, rutherfordium, dubnium, seaborgium, bohrium, hassium, meitnerium, darmstadtium, roentgenium, and copernicium. Preferably, the star polymer contains no detectable amount of any of the above restricted metals. No restriction is placed on the concentration of boron, silicon, or any individual alkali metal in the chemical formula of a star polymer, providing the star polymer and the loaded star polymer have desirable properties (e.g., amphiphilic properties). The molecular formula of a cargo material (e.g., cholesterol-lowering drug and/or nutraceutical) can comprise a restricted metal.

The star polymer can be biodegradable, partially biodegradable, or non-biodegradable. The term "biodegradable" is defined by the American Society for Testing and Materials as a degradation caused by biological activity, especially by enzymatic action, leading to a significant change in the chemical structure of the material. For purposes herein, a material is biodegradable if it undergoes 60% biodegradation within 180 days in accordance with ASTM D6400.

Non-limiting examples of cholesterol-lowering agents include simvastatin, lovastatin, atorvastatin, fluvastatin, pitavastatin, pravastatin, and rosuvastatin, whose structures are listed below.

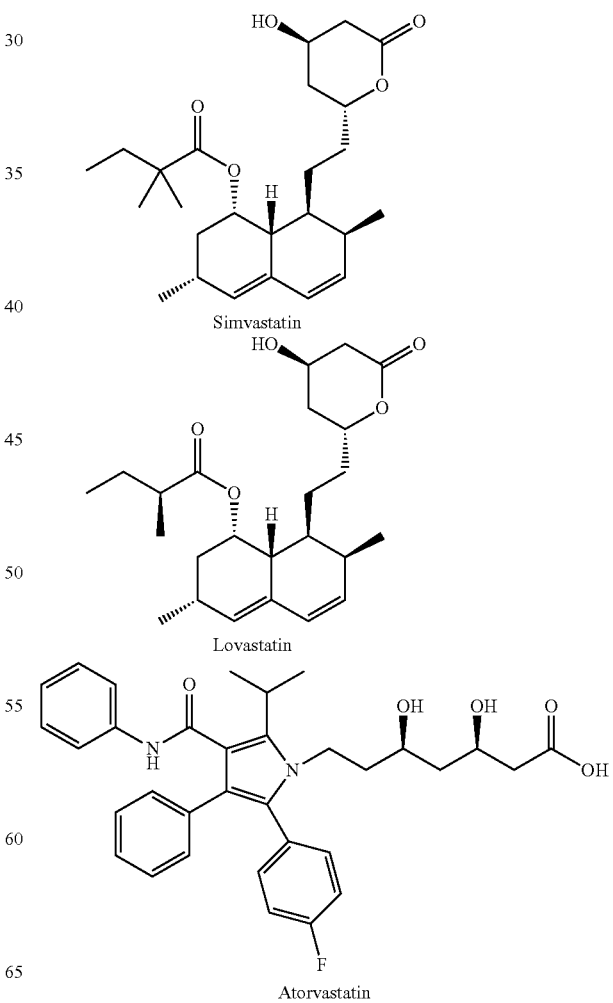

Simvastatin

Lovastatin

Atorvastatin

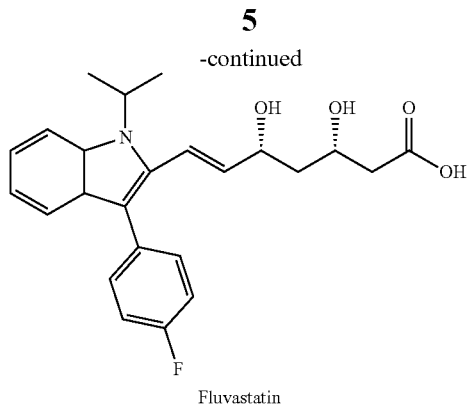
Fluvastatin

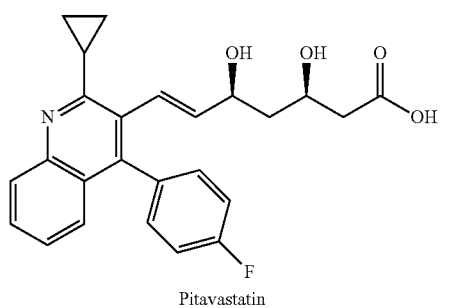
Pitavastatin

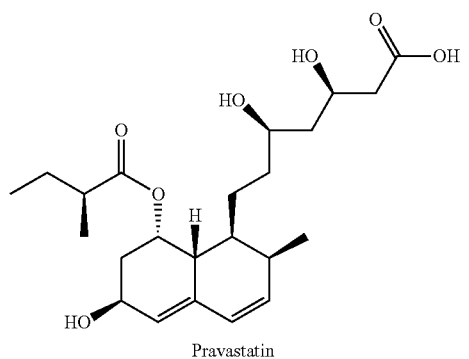
Pravastatin

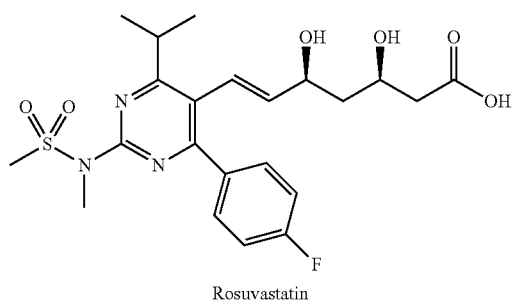
Rosuvastatin

The cholesterol-lowering agents can be used singularly or in combination when preparing a loaded star polymer. In an embodiment, the cholesterol-lowering agent is simvastatin.

Exemplary non-limiting nutraceuticals include ubiquinone (Coenzyme Q10, or CoQ10), menadione, duroquinone, idebenone, and decylubiquinone, whose structures are listed below.

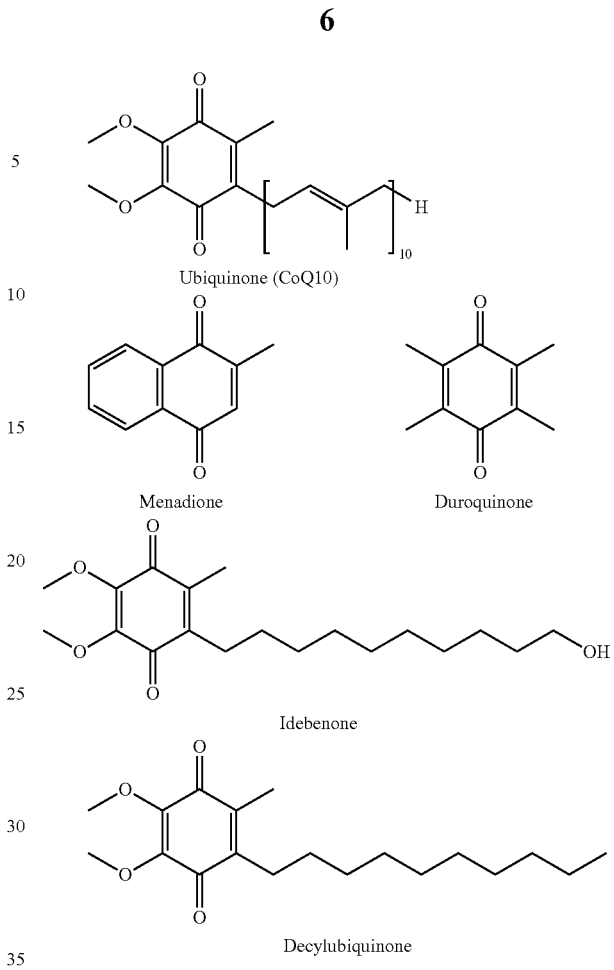

The nutraceuticals can be used singularly or in combination when preparing a loaded star polymer. In an embodiment, the nutraceutical is ubiquinone (CoQ10).

The loaded star polymers can comprise other cargo materials. Exemplary other cargo materials include biomolecules (e.g., DNA, genes, peptides, proteins, enzymes, lipids, phospholipids, and nucleotides), natural or synthetic organic compounds (e.g., drugs, dyes, synthetic polymers, oligomers, vitamins, and amino acids), inorganic materials (e.g., metals and metal oxides), chromophores that aid in diagnostics (e.g., porphyrinoid compounds, including porphyrins and phthalocyanines), radioactive variants of the foregoing, and combinations of the foregoing. The cargo material can comprise a metal, including one or more of the above-described restricted metals.

Preparation of Star Polymers

For simplicity, all examples herein assume the ideal case that all initiating groups react and, therefore, the length of polymeric blocks may be described by the division of the number of moles of monomer units (e.g., x, y, z, etc.) by the number of moles of initiating sites. However, the reaction of 100% of the initiating sites is not a requirement for successful implementation of the invention. Non-reacted initiating groups can serve as additional reaction or initiator sites during subsequent synthetic processes. Therefore, it is advantageous that a high percentage of the initiating groups initiate the polymerization reaction.

No restriction is placed on the method of formation of the polymer arms and the core. The amphiphilic arms and the polymer core can be produced by polymerization of a vinyl monomer, by a ring opening polymerization of a cyclic carbonyl monomer, or by employing a combination of different polymerization techniques, examples of which are illustrated below.

The star polymers are represented by the general formula (1):

wherein w' is a positive integer equal to 6 or more, more specifically 6-100,

C' represents the crosslinked polymer core (i.e., core) and has a valency of w', and each P' represents an independent amphiphilic polymer arm.

The star polymer comprises w' number of polymer arms P', which are covalently linked to and emanate from the core C'. Each of the 6 or more polymer arms comprises a hydrophobic polymer block A and a peripheral hydrophilic polymer block B. The polymer arms and the core can independently comprise a homopolymer chain segment comprising a given repeat unit and/or a random copolymer chain segment comprising two or more repeat units of different chemical structure.

The repeat units of the polymer arms can comprise one or more side chain functional groups for adjusting the binding and release properties of the star polymer. Exemplary non-limiting side chain functional groups include urea groups, carboxylic ester groups, carboxylic acid groups, carboxylic acid salts, latent carboxylic acid groups, quaternary amine groups, tertiary amine groups, secondary amine groups, primary amine groups, azides, alkynes, poly(alkylene ether) groups, and combinations thereof. Particularly useful side chain functional groups are amine groups capable of undergoing a protonation and/or deprotonation at a pH suitable for releasing a cargo material.

Star Polymers Prepared by Vinyl Polymerizations

Vinyl polymerization methods are well known and include but are not limited to free radical polymerizations, living anionic addition polymerizations, and living free radical polymerizations (e.g., nitroxide mediated radical polymerization (NMP), atom radical transfer polymerization (ATRP), and reversible addition-fragmentation chain transfer (RAFT)).

Exemplary vinyl monomers include styrene and substituted styrenes, divinylbenzene and substituted divinylbenzenes, (meth)acrylate esters, ethylene glycol di(meth)acrylates, (meth)acrylamides, acrylonitrile, vinyl acetate, vinyl chloride, ethene, propene, and butadiene. Other vinyl monomers will be readily apparent to those skilled in the polymer art.

Anionic addition polymerizations of vinyl monomers (e.g., styrene, propene, butadiene), are typically initiated by nucleophilic alkyllithium compounds, Grignard reagents, metal alkoxides and metal hydroxides. The resulting anionic living polymer chain generally have low polydispersity but are typically non-biodegradable. Scheme 1 illustrates formation of a crosslinked core linked to 6 or more intermediate polymer arms formed by anionic polymerization of a polymerizable vinyl monomer. Vinyl monomer (5) is optional.

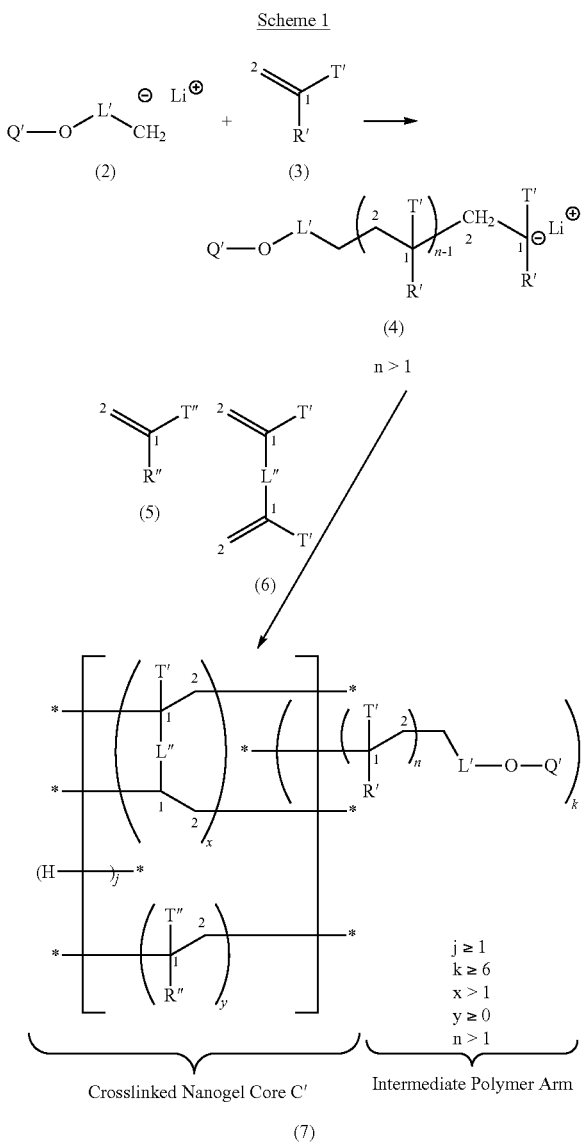

wherein:
carbons 1 and 2 of the vinyl groups and any single bonds derived therefrom are labeled,
n and x are independent positive numbers representing average degree of polymerization, and each of n and x has a value greater than 1,
y is a number representing average degree of polymerization, and y has a value greater than or equal to 0,
j is a positive number representing average number of terminal hydrogen end groups of the core, and j has an average value of 1 or more,
k is a positive number representing average number of intermediate polymer arms, and k has a value of 6-100,
L' is a $C_1$-$C_{20}$ linking group,
L" is a single bond or a divalent $C_1$-$C_{20}$ linking group,
Q' is an alcohol protecting group,
each R' is an independent monovalent $C_1$-$C_{20}$ radical, and each T' is an independent monovalent radical selected from the group consisting of hydrogen and methyl,
each R" is an independent monovalent $C_1$-$C_{20}$ radical, and each T" is an independent monovalent radical selected from the group consisting of hydrogen and methyl.

Anionic materials (2) can initiate chain growth by addition of the anionic carbon to carbon 2 of the vinyl monomer (3). The resulting polymer (4) is a living anionic polymer, which is capable of initiating a second polymerization of a mixture of vinyl monomer (6) and optional vinyl monomer (5) to the form the crosslinked core C' of (7). The precursor star polymer of (7) comprises an intermediate polymer arm comprising a protected alcohol group (*—O-Q').

The notation of Scheme 1 is as follows. The vertical stacking of the repeat units enclosed within the square brackets of (7) indicates a random distribution of these covalently linked repeat units in the crosslinked polymer chain of the core. Subscripts x and y indicate the average number of each of the respective repeat units of the core. An atomic center shown linked to an asterisk means the atomic center is covalently linked to another unspecified atomic center represented by the asterisk. Atomic centers outside the square brackets whose bond to an asterisk overlaps a given square bracket can be covalently linked to any atomic center within the square brackets that has a bond to an asterisk overlapping the same square bracket. For example, in the above structure, carbon labeled 1 of the terminal styrene repeat unit of each of the intermediate polymer arms can be linked to any carbon labeled 2 of the repeat units within the square brackets. Additionally, each of the j≥1 chain terminating hydrogens of the core can be linked to any carbon labeled 1 of the repeat units within the square brackets.

More specific mono-vinyl monomers (3) and (5) for an anionic polymerization include: styrene (T' and T"=H; R' and R"=phenyl); substituted styrenes (e.g., 4-methylstyrene, 4-methoxystyrene); vinyl esters (T' and T"=H, R' and R"=*—OC(=O)$R^a$, wherein $R^a$ is a $C_1$-$C_{20}$ group) such as, for example, vinyl acetate, vinyl propionate, vinyl butyrate; methacrylates (T' and T"=methyl and R' and R"=*—C(=O)O$R^b$, wherein $R^b$ is a $C_1$-$C_{20}$ group) such as, for example, methyl methacrylate, ethyl methacrylate, t-butyl methacrylate, and phenyl methacrylate; and vinyl ethers (T' and T"=H and R' and R"=*—$R^c$ wherein $R^c$ is a $C_1$-$C_{20}$ group) such as, for example, methylvinyl ether, ethylvinyl ether, and phenylvinyl ether. Vinyl monomers (3) and (5) can be the same or different vinyl monomers.

More specific divinyl monomers (6) for an anionic polymerization include divinyl benzene (T'=H, L"=1,4-phenylene) and ethylene glycol dimethacrylate (T'=Me, L"=*—C(=O)OCH$_2$CH$_2$O(O=)C—*).

In structure (7), the polymer chain having subscript n represents hydrophobic block A of the intermediate polymer arm. Scheme 2 below completes the formation of the block polymer arm from (7) using an ATRP polymerization.

Scheme 2

(7)

n > 1
k ≥ 6

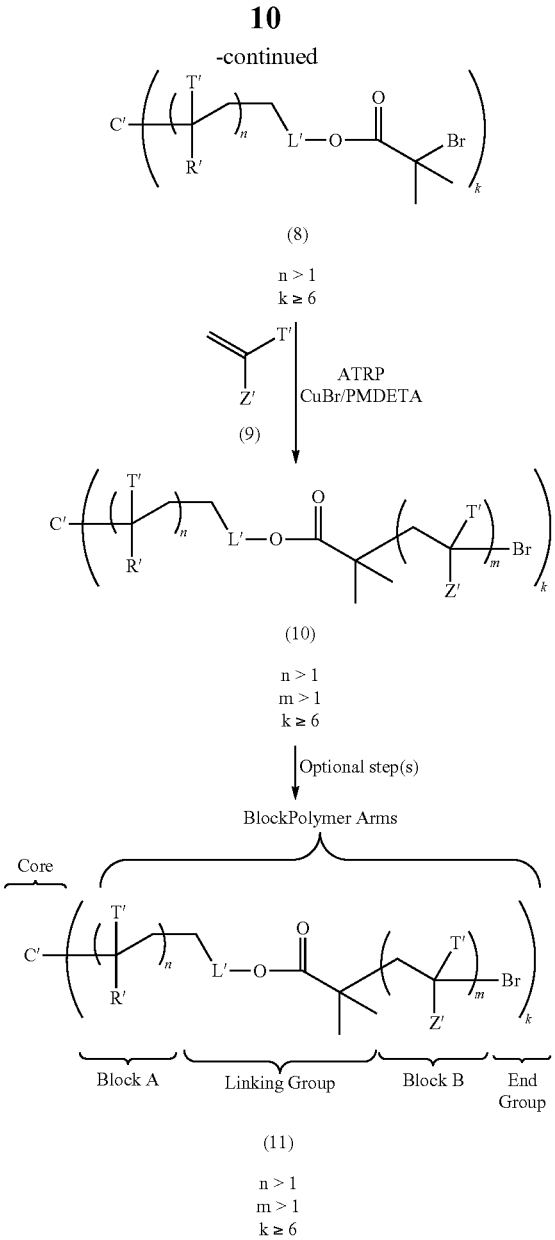

wherein:
C', L', Q', R', T', n, and k have the meanings described above,
m is a number representing average degree of polymerization, wherein m has a value between 1 and 1000,
Y' is a hydrophilic monovalent radical comprising a functional group selected from the group consisting of primary amine groups, secondary amine groups, tertiary amine groups, protonated forms of the foregoing amine groups, quaternary amine groups, carboxylic ester groups, carboxylic acid groups, carboxylate groups, alcohol groups, and combinations of the foregoing groups, and
Z' is a monovalent radical equal to Y' or a precursor thereof.

The ATRP polymerization is typically initiated by an alkyl halide (e.g., structure (8)) and is catalyzed by a transition metal (e.g., CuBr). N,N,N',N,N-Pentamethyldiethylenetriamine (PMDETA) is typically used as a stabilizing ligand. ATRP produces polymers having narrow molecular distributions. Common monomers for ATRP include (meth)acrylates, (meth)acrylamides, acrylonitrile, and styrenes.

Non-limiting examples of Z' precursors of Y' include reactive halide groups (e.g., alkyl halides, benzyl halides comprising chloride, bromide, and/or iodide) capable of reacting with a tertiary amine to form a quaternary amine group; protected (latent) carboxylic acid groups (e.g., tetrahydropyranyl (THP) ester, trimethyl silyl ester, t-butyl ester, benzyl ester, methyl ester, acetal ester) that when deprotected release a carboxylic acid; protected primary and secondary amine groups (e.g., tert-butyloxy carbamates, benzyloxy carbamates, vinyloxy carbamates, allyloxy carbamates) that when deprotected release the respective primary and secondary amine group; and protected alcohol groups (e.g., THP ethers, trimethyl silyl ethers, benzyl ethers, trityl ethers) that when deprotected release a respective alcohol group.

Herein, a quaternary amine group comprises a positive-charged nitrogen that is covalently bonded only to carbon (i.e., 3 or 4 carbons) and is ionically associated with a negative-charged counterion (e.g., bromide ion, chloride ion, iodide ion, acetate ion).

In an embodiment, Z' is the same as Y'. Exemplary non-limiting monomers (9) wherein Z' is the same as Y' include acrylic acid, methacrylic acid, 2-hydroxyethyl methacrylate, 3-hydroxypropyl methacrylate, di(ethylene glycol) methyl ether methacrylate, 2-aminoethyl methacrylate, 3-aminopropyl methacrylate, 2-(N,N-dimethylamino)ethyl methacrylate (DMAEMA), 2-(N,N-diethylamino)ethyl methacrylate, 2-(N,N-diisopropylamino)ethyl methacrylate, vinyl pyridine, vinyl imidazole, 4-dimethylamino styrene.

Star Polymers Prepared by Ring Opening Polymerization

Biodegradable or partially biodegradable star polymers can be formed using a ring opening polymerization (ROP) of cyclic carbonate and/or cyclic ester monomer(s) to form the polymer arms and/or the core. The ROP preferably employs an organocatalyst whose chemical formula comprises none of the above-described restricted metals.

Star polymers formed by organocatalyzed ring opening polymerizations of cyclic carbonyl monomers generally have narrower molecular weight distributions (i.e., low polydispersity indexes) and are more biocompatible (i.e., non-immunogenic, non-cytotoxic material) compared to ROP polymers prepared with metal catalysts due to generally higher levels of metal contaminants in the latter materials. The living end groups of ROP polymers can initiate a new ROP, allowing in some instances for sequential ROP polymerizations to be conducted in a single vessel.

Scheme 3 illustrates the preparation of a biodegradable amphiphilic star polymer by organocatalyzed ring opening polymerization. In this example, the polymer arm is prepared first followed by the core.

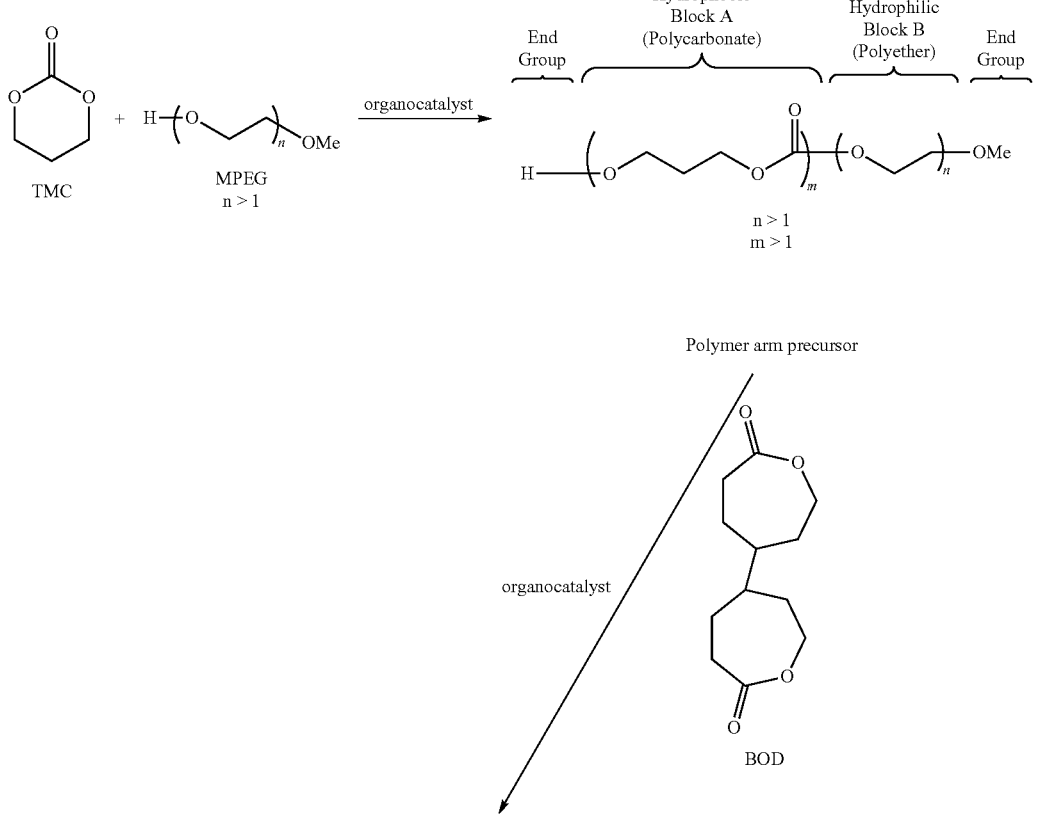

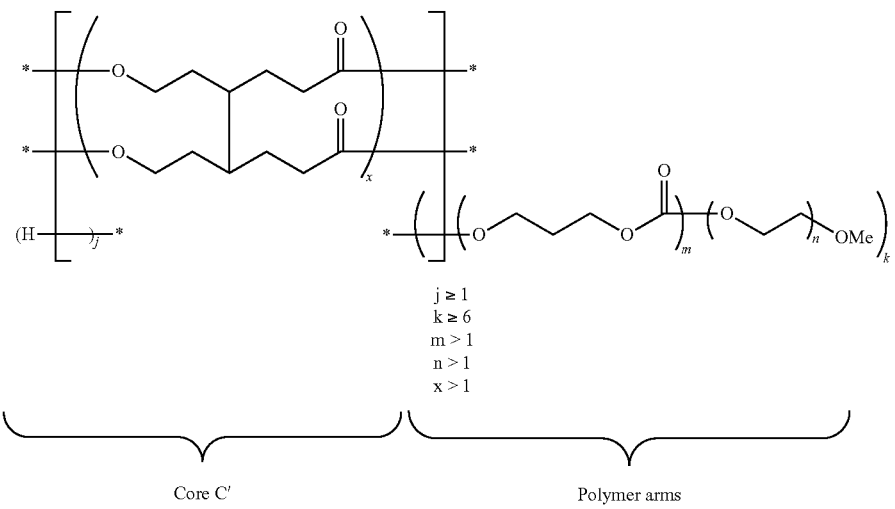

Core C'  Polymer arms

The mono-methyl poly(ethylene glycol) (MPEG) initiates ROP of trimethylene carbonate (TMC) in the presence of a suitable organocatalyst, thereby producing the polymer arm precursor. The polymer arm precursor is a diblock copolymer comprising a living end group (nucleophilic alcohol group), which is capable of initiating another ROP to form the crosslinked core. The polymer arm precursor comprises a hydrophobic polycarbonate block A derived from TMC, and a hydrophilic polyether block B. The second ring opening polymerization of 5,5'-bis(oxepanyl-2-one) (BOD), a crosslinking bis-cyclic ester monomer, produces a star polymer comprising a crosslinked polyester core covalently linked to 6 or more polycarbonate-polyether block polymer arms. The formation of the core can include a monofunctional co-monomer.

The polymer arm precursor can be chemically modified to introduce additional functionality before or after formation of the core. For example, the reaction mixture can comprise one or more latent hydrophobic cyclic carbonyl monomers, from which a hydrophobic repeat unit can be derived by a chemical transformation after a ring opening polymerization. Similarly, the reaction mixture can comprise one or more latent hydrophilic cyclic carbonyl monomers, from which a hydrophilic repeat unit can be derived by a chemical transformation after a ring opening polymerization. Scheme 4 illustrates an organocatalyzed ROB involving step-wise construction of the hydrophilic block B. In this example, a polymer arm precursor is prepared first comprising a precursor block B, followed by the core. In a third step, the precursor block B is converted to a hydrophilic block B by reaction with a tertiary amine.

Scheme 4

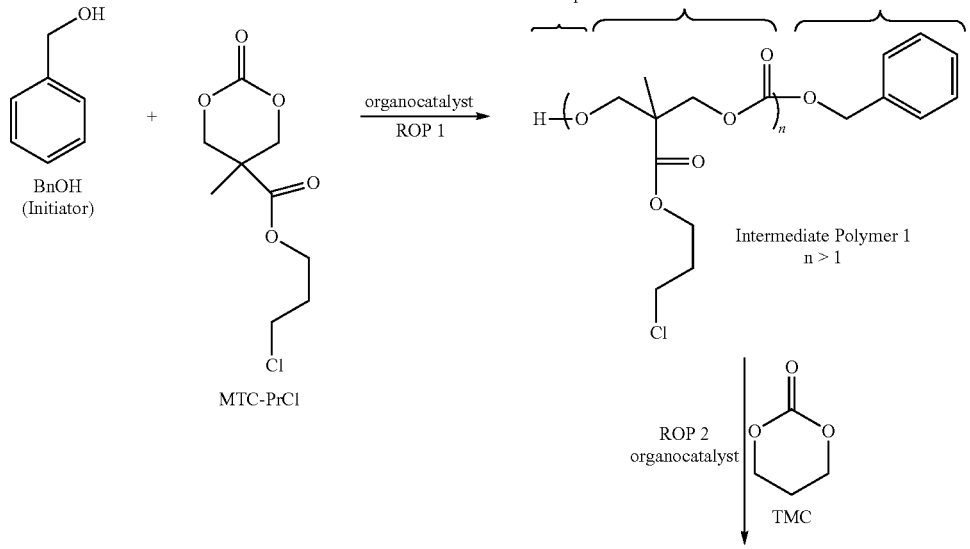

-continued
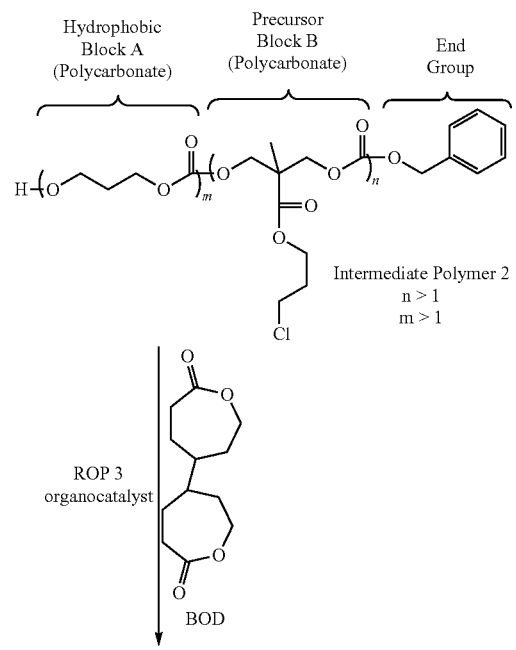
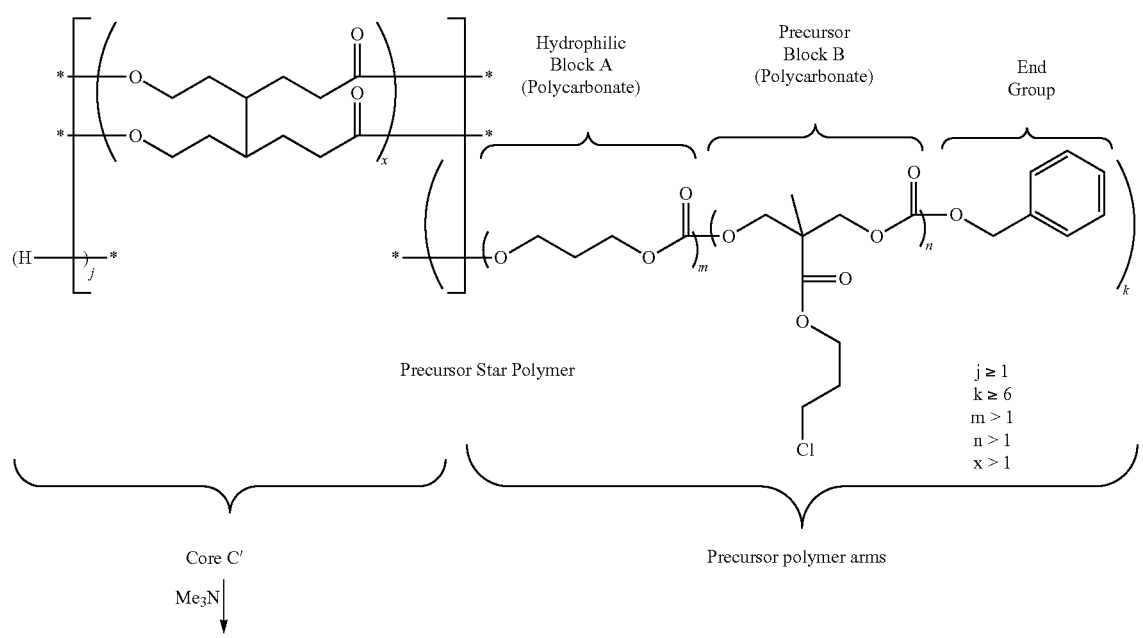

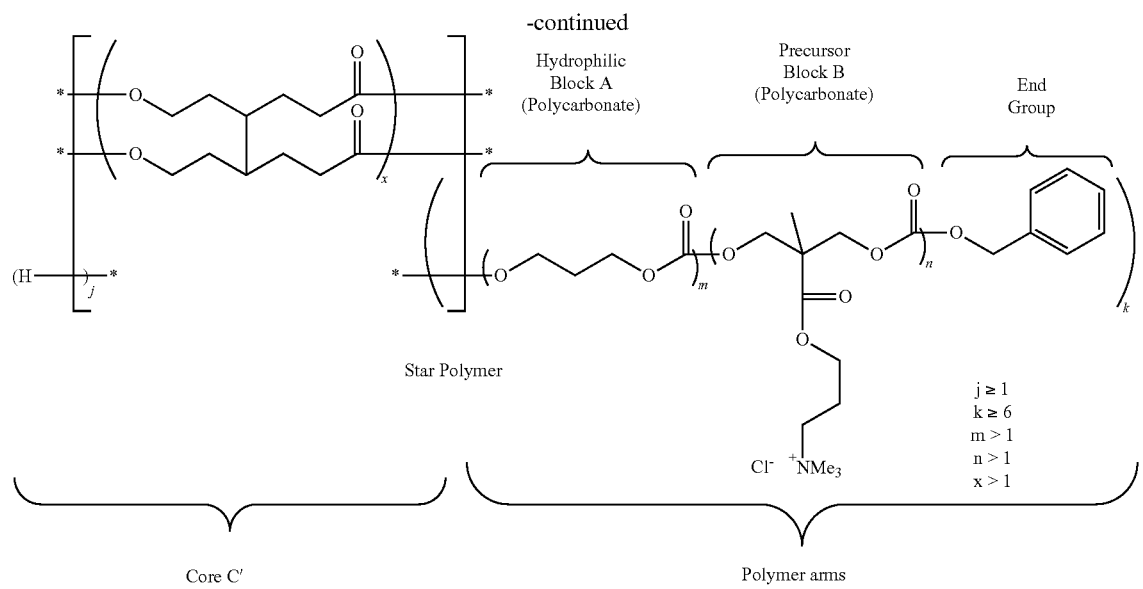

In the example of Scheme 4, benzyl alcohol (BnOH) initiates the first ROP of MTC-Cl, forming intermediate polymer 1 containing a precursor block B, which has a pendent reactive chloride. Intermediate polymer 1 initiates a second ROP with trimethylene carbonate (TMC), thereby producing intermediate polymer 2 comprising two polycarbonate blocks in the polymer arms. Intermediate polymer 2 initiates a third ROP with bis-cyclic ester BOD, forming precursor star polymer comprising a crosslinked polyester core. Lastly, treating precursor star polymer with trimethylamine forms the amphiphilic star polymer. The star polymer comprises a hydrophobic polycarbonate block A covalently linked to the polyester core and a peripheral hydrophilic cationic polycarbonate block B having a pendent quaternary amine group.

The above synthetic schemes demonstrate methods of forming amphiphilic star polymers are meant to be illustrative and not limiting. No restriction is placed on the order of formation of the core, block A, and block B. The core, block A, and block B can be formed in any order, stepwise or simultaneously with one another, using polymeric and/or non-polymeric starting materials.

The polymer arm and/or the core can comprise optional end cap groups (ECG). End cap groups can impart stability and useful functionality to the star polymer structure. End capping agents are numerous, and methods of their use are well established in the polymer art. End capping agents can be selected based on the functionality desired and their intended use. The optional end cap group can comprises a moiety selected from the group consisting of alkyl ester groups, aryl ester groups, poly(alkylene ether) groups (e.g., poly(alkylene oxide)), thiol groups, amine groups, carboxylic acid groups, quaternary amine groups, functional groups capable of targeting specific cell types, and combinations thereof. For example, the polymer arms can comprise a peripheral galactose-containing end group for targeting liver cells. In another example, the polymer arms can comprise peripheral mannose-containing end group for binding mannose-specific proteins.

Cyclic Carbonyl Monomers

Crosslinking monomers for forming the core by a ring opening polymerization include multi-functional cyclic esters and cyclic carbonates. The crosslinking monomer can contain two or more cyclic carbonyl rings capable of ROP.

Non-limiting exemplary bis-cyclic esters include the following compounds.

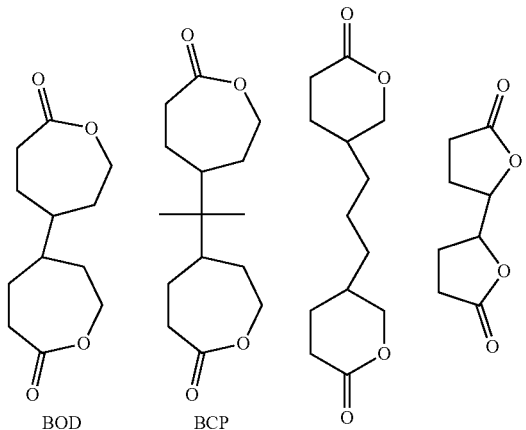

The polymer arms are prepared from mono-functional cyclic carbonyl monomer (i.e., those containing one cyclic carbonyl ring capable of ROP).

Non-limiting exemplary mono-functional cyclic ester monomers (e.g., lactones) include compounds of Table 1.

TABLE 1

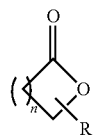

R = H; n = 1: beta-Propiolactone (b-PL)
R = H; n = 2: gamma-Butyrolactone (g-BL)
R = H; n = 3: delta-Valerolactone (d-VL)
R = H; n = 4: epsilon-Caprolactone (e-CL)
R = CH$_3$; n = 1: beta-Butyrolactone (b-BL)
R = CH$_3$; n = 2: gamma-Valerolactone (g-VL)

TABLE 1-continued
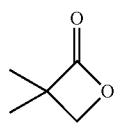
Pivalolactone
(PVL)
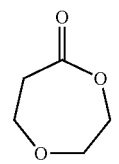
1,5-Dioxepan-2-one
(DXO)
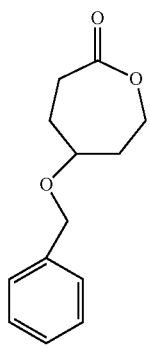 [SMILES: O=C1CCC(OCc2ccccc2)CCO1]
5-(Benzyloxy)oxepan-2-one
(BXO)
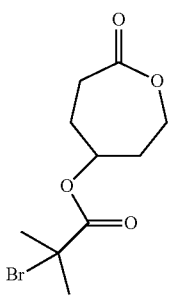
7-Oxooxepan-4-yl 2-bromo-2-
methylpropanoate
(BMP-XO)
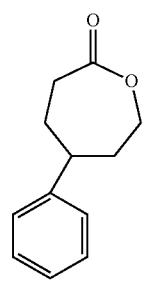 [SMILES: O=C1CCC(c2ccccc2)CCO1]
5-Phenyloxepan-2-one
(PXO)
TABLE 1-continued
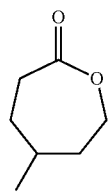
5-Methyloxepan-2-one
(MXO)
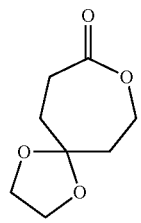 [SMILES: O=C1CCC2(CCO1)OCCO2]
1,4,8-Trioxa(4,6)spiro-9-undecane
(TOSUO)
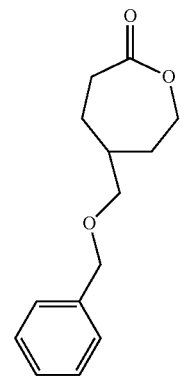 [SMILES: O=C1CCC(COCc2ccccc2)CCO1]
5-(Benzyloxymethyl)oxepan-2-one
(BOMXO)
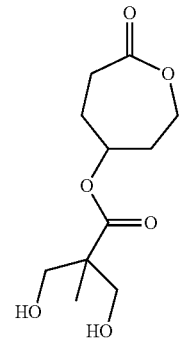 [SMILES: CC(CO)(CO)C(=O)OC1CCOC(=O)CC1]
7-Oxooxepan-4-yl 3-hydroxy-2-
(hydroxymethyl)-2-methylpropanoate
(OX-BHMP)
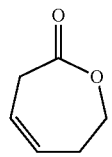
(Z)-6,7-Dihydrooxepin-2(3H)-one
(DHXO)

Other mono-functional cyclic ester monomers are dioxane dicarbonyl monomers of Table 2.

TABLE 2

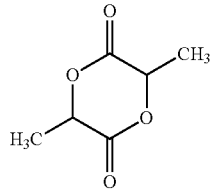

D-Lactide (DLA),
L-Lactide (LLA), or
racemic Lactide, 1:1 D:L forms (DLLA)

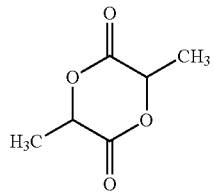

meso-Lactide (MLA)
(two opposite centers of asymmetry,
R and S)

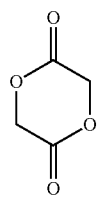

Glycolide (GLY)

Non-limiting examples of mono-functional cyclic carbonate monomers are listed in Table 3.

TABLE 3

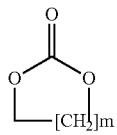

m = 1: Trimethylene carbonate (TMC)
m = 2: Tetramethylene carbonate (TEMC)
m = 3: Pentamethylene carbonate (PMC)

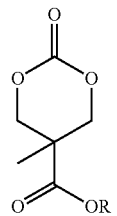

R = methyl (MTCOMe)
R = t-butyl (MTCO$^t$Bu)
R = ethyl (MTCOEt)

TABLE 3-continued

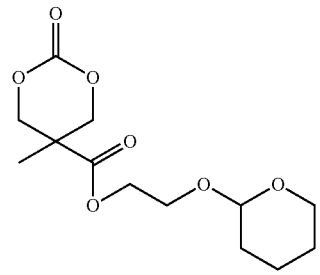 [SMILES: CC1(C(=O)OCCOC2CCCCO2)COC(=O)OC1]

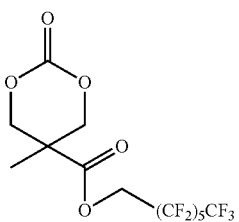

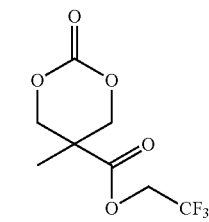 [SMILES: CC1(C(=O)OCC(F)(F)F)COC(=O)OC1]

(MTCTFE)

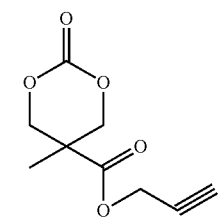

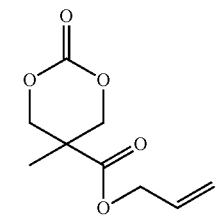

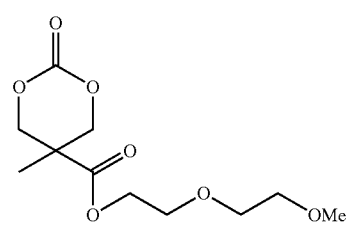 [SMILES: COCCOCCOC(=O)C1(C)COC(=O)OC1]

TABLE 3-continued
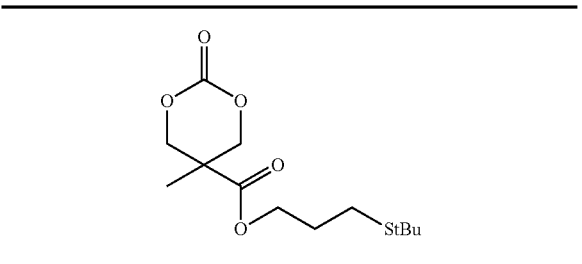
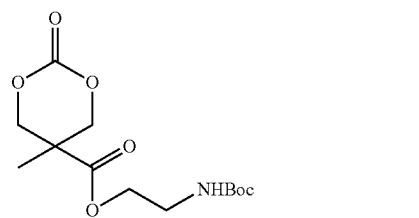 [SMILES: CC(C)(C)OC(=O)NCCOC(=O)C1(C)COC(=O)OC1]
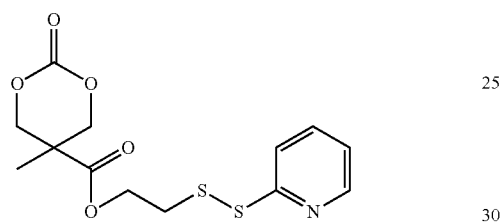
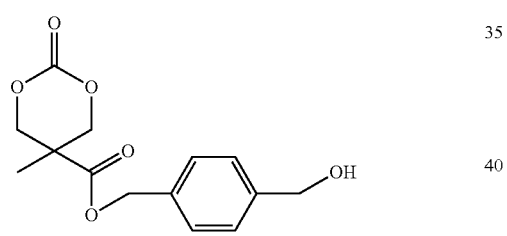
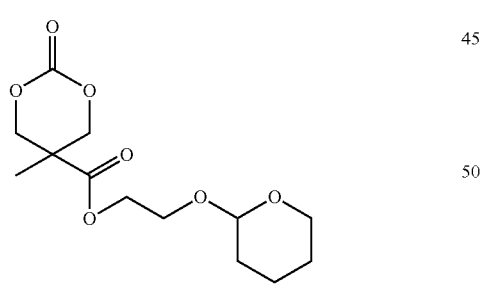
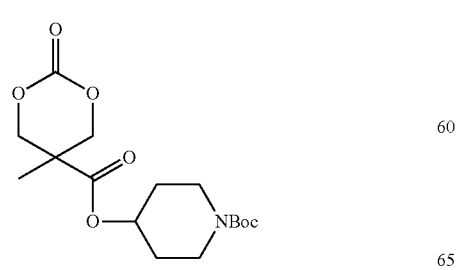
TABLE 3-continued
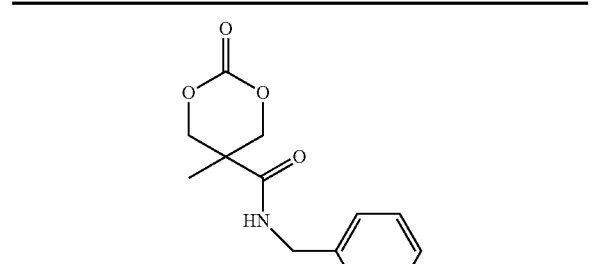
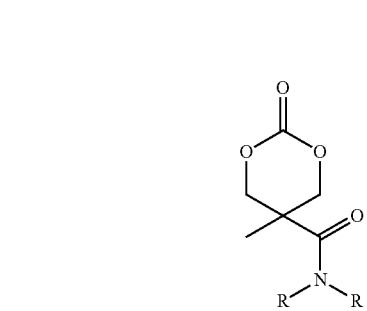
R = methyl
R = iso-propyl
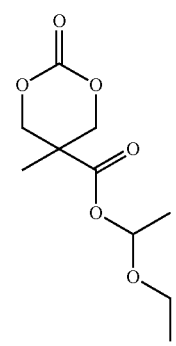 [SMILES: CCOC(C)OC(=O)C1(C)COC(=O)OC1]
(MTCOEE)
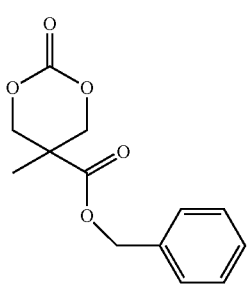 [SMILES: CC1(C(=O)OCc2ccccc2)COC(=O)OC1]
(MTCOBn)

TABLE 3-continued

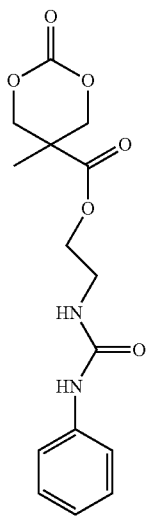 [SMILES: CC1(C(=O)OCCNC(=O)Nc2ccccc2)COC(=O)OC1]

MTCU

The cyclic carbonyl monomer can comprise a pendent protected carboxylic acid group, which after the ROP can be deprotected to form a carboxylic acid group of the ROP polymer side chain. Non-limiting examples of protected carboxylic acids include esters that can be hydrolyzed under mild conditions (e.g., trifluoroethyl ester, pentafluorophenyl ester, or p-nitrophenyl ester, N-hydroxysuccinimimide ester, trimethylsilyl ester, tetrahydropyranyl ester). Other protected carboxylic acids include thermally labile tertiary esters (e.g., t-butyl esters). Still other latent carboxylic acids include esters capable of being reductively cleaved using hydrogen and a suitable catalyst (e.g., benzyl esters, cleavable by $H_2$/Pd—C). One example is the benzyl ester of MTCOBn.

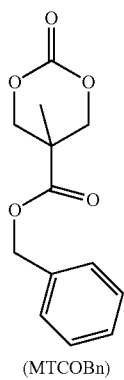

(MTCOBn)

The benzyl ester of MTCOBn can be cleaved to a carboxylic acid using $H_2$/Pd—C after the ring opening polymerization. In an embodiment, the protected carboxylic acid group is any carboxylic ester that can be converted to a carboxylic acid group without causing undesirable chemical alteration of the polymer.

Another example of a protected carboxylic acid group is an acetal-protected carboxylic acid group, herein also referred to as an acetal ester group. The acetal ester group has the general formula (12):

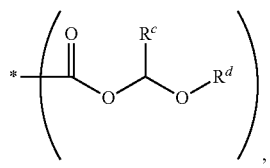

(12)

wherein $R^c$ and $R^d$ are monovalent radicals independently comprising from 1 to 20 carbons. In an embodiment, $R^c$ is methyl and $R^d$ is ethyl. An example of cyclic carbonate compound comprising an acetal ester is MTCOEE:

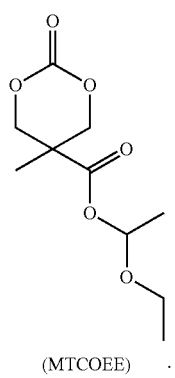 [SMILES: CCOC(C)OC(=O)C1(C)COC(=O)OC1]

(MTCOEE)

Repeat units derived from MTCOEE comprise aside chain acetal ester that is readily deprotected by acid (e.g., in the acidic endosomal environment of a cell). The resulting carboxylic acid groups of the cationic polymer can be deprotonated at pH 6-7 (e.g., in the cytoplasm of a cell).

The cyclic carbonyl monomers can comprise a reactive monovalent leaving group that when treated with a tertiary amine, produces a quaternary amine. Reactive monovalent leaving groups include alkyl halides (e.g., alkyl chlorides, alkyl bromides, or alkyl iodides), sulfonate esters (e.g., tosylates, or mesylates), epoxides, and oxetanes.

Mono-functional cyclic carbonate monomers comprising a reactive halide leaving group are listed in Table 4.

TABLE 4

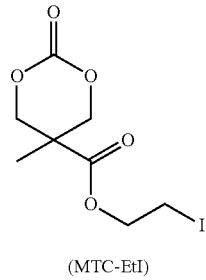

(MTC-EtI)

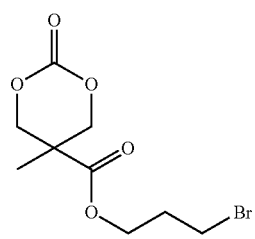

TABLE 4-continued (MTC-PrBr)

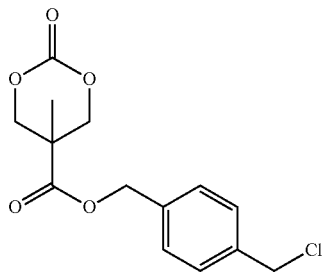

(MTC-BnCl)

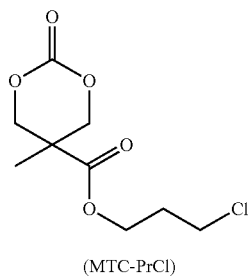

(MTC-PrCl)

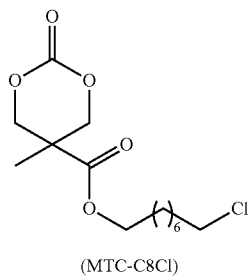

(MTC-C8Cl)

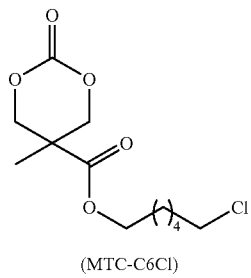

(MTC-C6Cl)

Reaction of the leaving group with a tertiary amine to form a quaternary amine is generally performed after the ring opening polymerization when the leaving group occupies a side chain position of the ROP polymer.

The tertiary amine used to form a quaternary amine group can comprise a single nitrogen such as a trialkylamine, including but not limited to trimethylamine, triethylamine, tripropylamine, and the like. The tertiary amine can further comprise additional functional groups, in particular a carboxylic acid group, for example 3-(N,N-dimethylamino) propionic acid. In such instances, the cationic polymer will comprise repeat units comprising a side chain moiety comprising a quaternary amine group and a carboxylic acid group.

The tertiary amine can also comprise isotopically enriched versions of the tertiary amine, such as trimethyl-amine-$^{14}$C, trimethylamine-$^{15}$N, trimethylamine-$^{15}$N, trimethyl-$^{13}$C$_3$-amine, trimethyl-d$_9$-amine, and trimethyl-d$_9$-amine-$^{15}$N. The tertiary amine can also comprise a radioactive moiety suitable for targeting a specific cell type, such as a cancer cell.

The tertiary amine can be a bis-tertiary amine of the general formula (13):

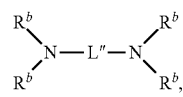

(13)

where L" is a divalent linking group comprising 2 to 30 carbons, and each monovalent $R^b$ group is independently selected from functional groups comprising 1 to 30 carbons. Each $R^b$ group can independently be branched or non-branched. Each $R^b$ group can independently comprise an alkyl group, aryl group, ketone group, aldehyde group, hydroxyl group, alkene group, alkyne group, cycloaliphatic ring comprising 3 to 10 carbons, heterocylic ring comprising 2 to 10 carbons, ether group, amide group, ester group, and combinations of the foregoing functional groups. The heterocyclic ring can comprise oxygen, sulfur and/or nitrogen. Two or more $R^b$ groups can also together form a ring. Representative L" groups include *—(CH$_2$)$_{z'}$—* where z' is an integer from 2 to 30, *—(CH$_2$CH$_2$O)$_{z''}$CH$_2$CH$_2$—* where z" is an integer from 1 to 10, *—CH$_2$CH$_2$SCH$_2$CH$_2$—*, *—CH$_2$CH$_2$SSCH$_2$CH$_2$—*, *—CH$_2$CH$_2$SOCH$_2$CH$_2$—*, and *—CH$_2$CH$_2$SO$_2$CH$_2$CH$_2$—*. L" can further comprise a monovalent or divalent cycloaliphatic ring comprising 3 to 20 carbons, a monovalent or divalent aromatic ring comprising 6 to 20 carbons, a ketone group, aldehyde group, hydroxyl group, alkene group, alkyne group, a heterocylic ring comprising 2 to 10 carbons, ether group, amide group, ester group, and combinations of the foregoing functional groups. The heterocyclic ring can comprise oxygen, sulfur and/or nitrogen. The bis-tertiary amine can also comprise isotopically enriched forms of the bis-tertiary amine, such as deuterium, carbon-13, and/or nitrogen-15 enriched forms thereof.

More specific bis-tertiary amines include N,N,N',N'-tetramethyl-1,2-ethanediamine (TMEDA), N,N,N',N'-tetramethyl-1,3-propanediamine (TMPDA), N,N,N',N'-tetramethyl-1,4-butanediamine (TMBDA), N,N,N',N'-tetraethyl-1,2-ethanediamine (TEEDA), N,N,N',N'-tetraethyl-1,3propanediamine (TEPDA), 1,4-bis(dimethylamino) cyclohexane, 1,4-bis(dimethylaminobenzene), N,N,N',N'-tetraethyl-1,4-butanediamine (TEBDA), 4-dimethylaminopyridine (DMAP), 4,4-dipyridyl-1,4-diazabicyclo[2.2.2]octane (DABCO), 4-pyrrolidinopyridine, 1-methylbenzimidazole, and combinations thereof. In an embodiment, the bis-tertiary amine is TMEDA.

The cyclic carbonyl monomers can also comprise isotopically enriched forms of the cyclic carbonyl monomers. These include functional groups comprising elements selected from the group consisting of $^{13}$C, $^{14}$C, $^{15}$N, deuterium, tritium, and combinations thereof. The cyclic carbonyl monomers can also comprise a radioactive moiety suitable for targeting a specific cell type, such as a cancer cell.

The cyclic carbonyl monomers can be purified by recrystallization from a solvent such as ethyl acetate or by other known methods of purification, with particular attention being paid to removing as much water as possible from the monomer. The monomer moisture content can be from 1 to 10,000 ppm, 1 to 1,000 ppm, 1 to 500 ppm, and most specifically 1 to 100 ppm, by weight of the monomer.

The polymers formed by ring-opening polymerization can have atactic, syndiotactic, or isotactic forms. The particular tacticity depends on the cyclic monomer(s), isomeric purity, and the reaction conditions.

The reaction mixture for the ring opening polymerization comprises one or more cyclic carbonyl monomers; a catalyst; an optional accelerator; an optional solvent, and an initiator. The ring opening polymerization is generally conducted in a reactor under inert atmosphere such as nitrogen or argon.

Less preferred catalysts for ring opening polymerizations include metal oxides such as tetramethoxy zirconium, tetra-iso-propoxy zirconium, tetra-iso-butoxy zirconium, tetra-n-butoxy zirconium, tetra-t-butoxy zirconium, triethoxy aluminum, tri-n-propoxy aluminum, tri-iso-propoxy aluminum, tri-n-butoxy aluminum, tri-iso-butoxy aluminum, tri-sec-butoxy aluminum, mono-sec-butoxy-di-iso-propoxy aluminum, ethyl acetoacetate aluminum diisopropylate, aluminum tris(ethyl acetoacetate), tetraethoxy titanium, tetra-iso-propoxy titanium, tetra-n-propoxy titanium, tetra-n-butoxy titanium, tetra-sec-butoxy titanium, tetra-t-butoxy titanium, tri-iso-propoxy gallium, tri-iso-propoxy antimony, tri-iso-butoxy antimony, trimethoxy boron, triethoxy boron, tri-iso-propoxy boron, tri-n-propoxy boron, tri-iso-butoxy boron, tri-n-butoxy boron, tri-sec-butoxy boron, tri-t-butoxy boron, tri-iso-propoxy gallium, tetramethoxy germanium, tetraethoxy germanium, tetra-iso-propoxy germanium, tetra-n-propoxy germanium, tetra-iso-butoxy germanium, tetra-n-butoxy germanium, tetra-sec-butoxy germanium and tetrat-t-butoxy germanium; halogenated compound such as antimony pentachloride, zinc chloride, lithium bromide, tin(IV) chloride, cadmium chloride and boron trifluoride diethyl ether; alkyl aluminum such as trimethyl aluminum, triethyl aluminum, diethyl aluminum chloride, ethyl aluminum dichloride and tri-iso-butyl aluminum; alkyl zinc such as dimethyl zinc, diethyl zinc and diisopropyl zinc; heteropolyacids such as phosphotungstic acid, phosphomolybdic acid, silicotungstic acid and alkali metal salt thereof; zirconium compounds such as zirconium acid chloride, zirconium octanoate, zirconium stearate and zirconium nitrate.

Metal from a polymerization catalyst can be entrapped by the crosslinked polymer core of the star polymer. The trapped metal can be cytotoxic and can interfere with the binding, release and/or the function of a cargo material and/or inorganic shell. Therefore, star polymers comprising a minimum of each restricted metal described further above is highly desirable.

Preferred catalysts for the ring opening polymerization are organocatalysts. An organocatalyst overcomes the problem of entrapped metal, in addition to providing a platform for synthesizing ring opened polymers of controlled, predictable molecular weights and narrow polydispersities.

The organocatalyst can be an organic acid. Exemplary organic acids include diphenylphosphate, sulfuric acid, p-toluenesulfonic acid, methanesulfonic acid, and trifluoromethane sulfonic acid (triflic acid). In an embodiment, the organocatalyst is trifluoromethane sulfonic acid.

The organocatalysts can be an organic base such as, for example, 4-dimethylaminopyridine, phosphines, N-heterocyclic carbenes (NHC), bifunctional aminothioureas, phosphazenes, amidines, and guanidines. In an embodiment the catalyst is N-(3,5-trifluoromethyl)phenyl-N'-cyclohexylthiourea (TU):

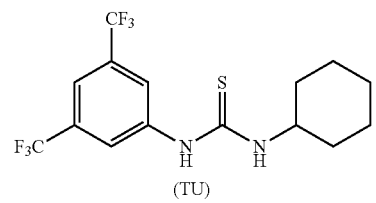

(TU)

Other organocatalysts comprise at least one 1,1,1,3,3,3-hexafluoropropan-2-ol-2-yl (HFP) group. Singly-donating hydrogen bond catalysts have the formula (14)

$$R^2-C(CF_3)_2OH \qquad (14)$$

$R^2$ represents a hydrogen or a monovalent radical having from 1 to 20 carbons, for example an alkyl group, substituted alkyl group, cycloalkyl group, substituted cycloalkyl group, heterocycloalkyl group, substituted heterocycloalkyl group, aryl group, substituted aryl group, or a combination thereof. Exemplary singly-donating hydrogen bonding catalysts are listed in Table 5.

TABLE 5

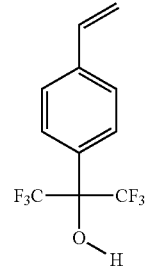 [SMILES: C=Cc1ccc(C(O)(C(F)(F)F)C(F)(F)F)cc1]

4-HFA-St

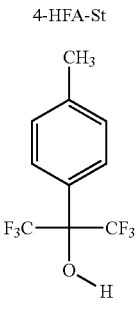

4-HFA-Tol

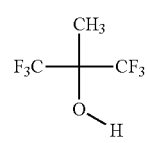

HFTB

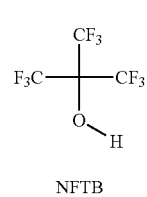

NFTB

TABLE 5-continued

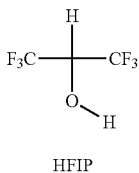

HFIP

Doubly-donating hydrogen bonding catalysts have two HFP groups, represented by the general formula (15):

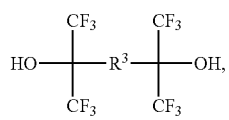
(15)

wherein R³ is a divalent radical bridging group containing from 1 to 20 carbons, such as an alkylene group, a substituted alkylene group, a cycloalkylene group, a substituted cycloalkylene group, a heterocycloalkylene group, substituted heterocycloalkylene group, an arylene group, a substituted arylene group, or a combination thereof. Representative double hydrogen bonding catalysts of formula (15) include those listed in Table 6. In a specific embodiment, $R^2$ is an arylene or substituted arylene group, and the HFP groups occupy positions meta to each other on the aromatic ring.

TABLE 6

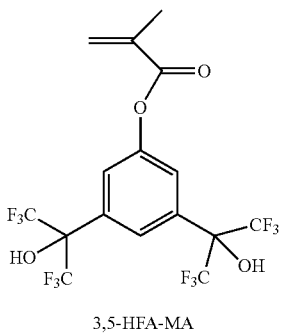

3,5-HFA-MA

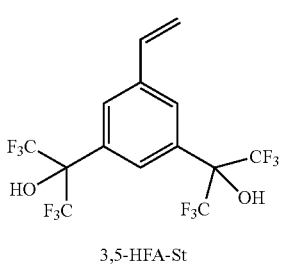

3,5-HFA-St

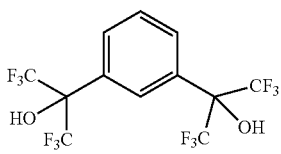 [SMILES: OC(c1cccc(C(O)(C(F)(F)F)C(F)(F)F)c1)(C(F)(F)F)C(F)(F)F]

1,3-HFAB

TABLE 6-continued

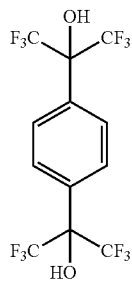

1,4-HFAB

Also contemplated are organocatalysts comprising HFP-containing groups bound to a support. In one embodiment, the support comprises a polymer, a crosslinked polymer bead, an inorganic particle, or a metallic particle. HFP-containing polymers can be formed by known methods including direct polymerization of an HFP-containing monomer (for example, the methacrylate monomer 3,5-HFA-MA or the styryl monomer 3,5-HFA-St). Functional groups in HFP-containing monomers that can undergo direct polymerization (or polymerization with a comonomer) include acrylate, methacrylate, alpha, alpha, alpha-trifluoromethacrylate, alpha-halomethacrylate, acrylamido, methacrylamido, norbornene, vinyl, vinyl ether, and other groups known in the art. Alternatively, pre-formed polymers and other solid support surfaces can be modified by chemically bonding an HFP-containing group to the polymer or support via a linking group. Examples of linking groups include $C_1$-$C_{12}$ alkyl, $C_1$-$C_{12}$ heteroalkyl, an ether group, a thioether group, an amino group, an ester group, an amide group, or a combination thereof. Also contemplated are catalysts comprising charged HFP-containing groups bound by ionic association to oppositely charged sites on a polymer or a support surface.

Other nitrogen base organocatalysts include triallylamine, triethylamine, tri-n-octylamine and benzyldimethylamine. Still other nitrogen base organocatalysts are listed in Table 7, including pyridine (Py), N,N-dimethylaminocyclohexane (Me₂NCy), 4-N,N-dimethylaminopyridine (DMAP), trans 1,2-bis(dimethylamino)cyclohexane (TMCHD), 1,8-diazabicyclo[5.4.0]undec-7-ene (DBU), 1,5,7-triazabicyclo[4.4.0]dec-5-ene (TBD), 7-methyl-1,5,7-triazabicyclo[4.4.0]dec-5-ene (MTBD), (−)-sparteine, (Sp) 1,3-bis(2-propyl)-4,5-dimethylimidazol-2-ylidene (Im-1), 1,3-bis(2,4,6-trimethylphenyl)imidazol-2-ylidene (Im-2), 1,3-bis(2,6-di-i-propylphenyl(imidazol-2-ylidene (Im-3), 1,3-bis(1-adamantyl)imidazol-2-ylidene (Im-4), 1,3-di-i-propylimidazol-2-ylidene (Im-5), 1,3-di-t-butylimidazol-2-ylidene (Im-6), 1,3-bis(2,4,6-trimethylphenyl)-4,5-dihydroimidazol-2-ylidene (Im-7), 1,3-bis(2,6-di-i-propylphenyl)-4,5-dihydroimidazol-2-ylidene, 1,3-bis(2,6-di-i-propylphenyl)-4,5-dihydroimidazol-2-ylidene (Im-8) or a combination thereof.

TABLE 7

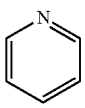

Pyridine

TABLE 7-continued (Py)

N,N-Dimethylaminocyclohexane
(Me2NCy)

4-N,N-Dimethylaminopyridine
(DMAP)

trans 1,2-Bis(dimethylamino)cyclohexane
(TMCHD)

1,8-Diazabicyclo[5.4.0]undec-7-ene
(DBU)

7-Methyl-1,5,7-triazabicyclo[4.4.0]dec-5-ene
(MTBD)

1,5,7-Triazabicyclo[4.4.0]dec-5-ene
(TBD)

(−)-Sparteine
(Sp)

TABLE 7-continued (Im-1)

1,3-Bis(2-propyl)-4,5-dimethylimidazol-2-ylidene (Im-2)

1,3-Bis(2,4,6-trimethylphenyl)imidazol-2-ylidene (Im-3)

1,3-Bis(2,6-di-i-propylphenyl(imidazol-2-ylidene (Im-4)

1,3-Bis(1-adamantyl)imidazol-2-yliden)

(Im-5)

1,3-Di-i-propylimidazol-2-ylidene (Im-6)

1,3-Di-t-butylimidazol-2-ylidene (Im-7)

1,3-Bis(2,4,6-trimethylphenyl)-4,5-dihydroimidazol-2-ylidene

TABLE 7-continued

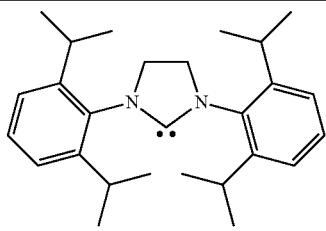

1,3-Bis(2,6-di-i-propylphenyl)-4,5-dihydroimidazol-2-ylidene
(Im-8)

The above-described nitrogen bases can be used alone as a catalyst when producing linear polymers by ring opening polymerization, such as the polymer arm precursor. Alternatively, the nitrogen bases can serve as an optional accelerator when used in combination with a primary catalyst, such as TU, in a ring opening polymerization. When employed as an accelerator, each nitrogen is potentially capable of participating as a Lewis base. In general, stronger nitrogen base accelerators improve the polymerization rate.

Exceptions to the above have been found when attempting to generate the polymer core by ring opening polymerization using base catalysis alone. In these instances, nitrogen bases comprising 1 or 2 nitrogens were not effective in forming unimolecular star polymers. The 1-nitrogen and 2-nitrogen base catalysts produced star polymers having high polydispersities (greater than 1.35), or products that were amorphous. Preferred nitrogen bases for the formation of the polymer core by ring opening polymerization of a bis-cyclic carbonyl monomer have three or more nitrogens. Unimolecular nano-sized amphiphilic star polymers having a polydispersity of 1.35 or less were successfully produced using this type of catalyst. One such base catalyst is 1,5,7-triazabicyclo[4.4.0]dec-5-ene (TBD). In some instances the star polymer can be formed using TBD as the sole catalyst. The star polymer can have a polydispersity index of 1.26, a hydrodynamic radius of 10.9 nm, and contains less than 100 ppm of any restricted metal.

The ROP reaction mixture comprises at least one catalyst and, when appropriate, several catalysts together. The ROP catalyst is added in a proportion of 1/20 to 1/40,000 moles relative to the cyclic carbonyl monomers, and preferably of 1/100 to 1/20,000 moles.

The ROP reaction mixture also comprises an initiator. The ROP polymer comprises a residue of the initiator that is covalently linked to an end group of the ring opened polymer chain grown therefrom. Initiators generally include nucleophiles such as alcohols, amines and thiols. The initiator can be monofunctional, difunctional, or multifunctional. The initiator can be polymeric or non-polymeric. For example, the initiator can be a polymeric alcohol, polymeric amine, or polymeric thiol.

More particularly, the initiator for the ring opening reaction is an alcohol. The alcohol initiator can be any suitable alcohol, including mono-alcohol, diol, triol, or other polyol, with the proviso that the choice of alcohol does not adversely affect the polymerization yield, polymer molecular weight, complexation with a biologically active material, and/or the desirable mechanical and physical properties of the star polymer. The alcohol can be multi-functional comprising, in addition to one or more hydroxyl groups, a halide, an ether group, an ester group, an amide group, or other functional group. Exemplary alcohols includes methanol, ethanol, propanol, butanol, pentanol, amyl alcohol, capryl alcohol, nonyl alcohol, decyl alcohol, undecyl alcohol, lauryl alcohol, tridecyl alcohol, myristyl alcohol, pentadecyl alcohol, cetyl alcohol, heptadecyl alcohol, stearyl alcohol, nonadecyl alcohol and other aliphatic saturated alcohols, cyclopentanol, cyclohexanol, cycloheptanol, cyclooctanol and other aliphatic cyclic alcohols; phenol, substituted phenols, benzyl alcohol, substituted benzyl alcohol, benzenedimethanol, trimethylolpropane, a saccharide, poly(ethylene glycol), propylene glycol, alcohol functionalized block copolymers derived from oligomeric alcohols, alcohol functionalized branched polymers derived from branched alcohols, or a combination thereof. Monomeric diol initiators include ethylene glycols, propylene glycols, hydroquinones, and resorcinols. An example of a diol initiator is BnMPA, derived from 2,2-dimethylol propionic acid.

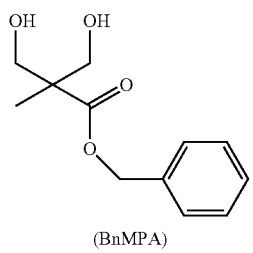 [SMILES: CC(CO)(CO)C(=O)OCc1ccccc1]

(BnMPA)

BnMPA is a precursor used in the preparation of cyclic carbonate monomers.

A ring-opening polymerization can be performed with or without the use of a solvent, preferably with a non-protic solvent. Non-limiting solvents include dichloromethane, chloroform, benzene, toluene, xylene, chlorobenzene, dichlorobenzene, benzotrifluoride, petroleum ether, acetonitrile, pentane, hexane, heptane, 2,2,4-trimethylpentane, cyclohexane, diethyl ether, t-butyl methyl ether, diisopropyl ether, dioxane, tetrahydrofuran, or a combination comprising one of the foregoing solvents. When a solvent is present, a suitable cyclic carbonyl monomer concentration is about 0.1 to 5 moles per liter, and more particularly about 0.2 to 4 moles per liter.

The ring-opening polymerization can be performed at a temperature that is about ambient temperature or higher, more specifically a temperature from 15° C. to 200° C., and more particularly 20° C. to 50° C. When the reaction is conducted in bulk, the polymerization is performed at a temperature of 50° C. or higher, and more particularly 100° C. to 200° C. Reaction times vary with solvent, temperature, agitation rate, pressure, and equipment, but in general the polymerizations are complete within 1 to 100 hours. The ROP reaction can be conducted at a temperature of about ambient temperature to about 200° C., preferably between 20° C. and 50° C.

Whether performed in solution or in bulk, the ring opening polymerizations are conducted in an inert, dry atmosphere. Generally, the ROP reaction mixture is maintained at a pressure of from 100 to 500 MPa (1 to 5 atm), more typically at a pressure of 100 to 200 MPa (1 to 2 atm) atmospheric pressure for 0.5 to 72 hours to effect complete consumption of cyclic carbonyl monomer. At the completion of the reaction, the solvent can be removed using reduced pressure.

The nitrogen base accelerator, when used, is present in an amount of 0.1 to 5.0 mol %, 0.1 to 2.5 mol %, 0.1 to 1.0 mol %, or 0.2 to 0.5 mol %, based on total moles of cyclic carbonyl monomer.

The amount of initiator for the ring opening polymerization is calculated based on the equivalent molecular weight per nucleophilic initiating group in the initiator (e.g., alcohol groups). The initiating groups are preferably present in an amount of 0.001 to 10.0 mol %, 0.1 to 2.5 mol %, 0.1 to 1.0 mol %, and 0.2 to 0.5 mol %, based on total moles of cyclic carbonyl monomer. For example, if the molecular weight of the initiator is 100 g/mole and the initiator has 2 hydroxyl groups, the equivalent molecular weight per hydroxyl group is 50 g/mole. If the polymerization calls for 5 mol % hydroxyl groups per mole of monomer, the amount of initiator is 0.05×50=2.5 g per mole of monomer.

In a specific embodiment, the catalyst is present in an amount of about 0.2 to 20 mol %, and the hydroxyl groups of the initiator are present in an amount of 0.1 to 5.0 mol % based on the equivalent molecular weight per nucleophilic group in the initiator.

As stated above, the ring opening polymerization forms a polymer chain comprising a living end group. The ROP polymer backbone can comprise a polyester homopolymer chain segment, a random polyester copolymer chain segment, a polycarbonate homopolymer chain segment, a random polycarbonate copolymer chain segment, or a random polyestercarbonate copolymer chain segment. The ROP polymer chain can comprise a terminal hydroxyl group, terminal thiol group, or terminal amine group, each of which can initiate further ROP chain growth, if desired.

Star Polymer Properties

The following properties pertain to any of the above-described star polymers, regardless of the method of polymerization.

The star polymers can have a number average molecular weight (Mn) as determined by size exclusion chromatography of at least 1000 g/mol, more specifically 1000 g/mol to 1,000,000 g/mol, and even more specifically 10,000 g/mol to 100,000 g/mol. In an embodiment, the star polymer has a number average molecular weight Mn of 10,000 to 20,000 g/mole. The star polymers also have a narrow polydispersity index (PDI), generally less than or equal to 2.0, more particularly from 1.01 to 1.35, even more particularly 1.1 to 1.30, and still more particularly 1.1 to 1.25.

A set of irregularly shaped three dimensional particles has an average circular cross-sectional diameter, which refers to the average of the minimum diameter of the circles cable of encompassing the respective particles when viewed from a top-down perspective. In aqueous solution, the star polymers disperse to form nano-sized particles having an average circular cross-sectional diameter of about 2 nm to about 500 nm, about 10 nm to about 250 nm, about 50 nm to about 200 nm, about 50 nm to about 150 nm, about 50 nm to about 120 nm, or about 50 nm to about 100 nm, as measured by dynamic light scattering. A given dispersed particle can comprise one or more macromolecules of star polymer. For the foregoing particle sizes, the aqueous solution can have a pH of from 5.0 to 8.0. This pH range can be increased for non-biodegradable compositions, such as those having a polymer core prepared from divinylbenzene. A given repeat unit of a star polymer can comprise no charge, a positive charge, a negative charge, or a mixture of positive and negative charges.

Loaded Star Polymers

Star polymer chemical structures can be used singularly or in combination when preparing a loaded star polymer.

The examples further below demonstrate that stepwise addition of the cargo materials to the star polymer in the order of nutraceutical followed by cholesterol-lowering drug results in improved cargo loading efficiencies of each cargo material compared to the results obtained using the inverse order of addition. Lower loading efficiencies were also observed for simultaneous addition of the cargo materials to the star polymer. The initial occlusion complex formed with the star polymer and the nutraceutical appears to have enhanced binding properties for the cholesterol lowering drug relative to the star polymer alone.

A preferred method of preparing a loaded star polymer comprises adding, with agitation, a first mixture comprising a disclosed nutraceutical and a first organic solvent to a second mixture comprising a disclosed star polymer and a second organic solvent, thereby forming a third mixture. In a next step, a fourth mixture comprising a disclosed cholesterol-lowering agent and a third organic solvent is added with agitation to the third mixture, thereby forming a fifth mixture. Lastly, water is added with agitation to the fifth mixture, thereby forming the loaded star polymer. In optional one or more steps, the loaded star polymer can be isolated by removal of the water and/or the first, second, and third organic solvents using well-known techniques. In an embodiment the first, second, and third organic solvents are water-miscible. In another embodiment, the first, second, and third organic solvents are the same solvent. In another embodiment, the solvent is THF.

Exemplary organic solvents for preparing loaded stars polymers include methanol, ethanol, propanol, 2-propanol, 1-butanol, 2-butanol, t-butyl alcohol, acetone, 2-butanone, dimethoxyethane, diglyme, diethyl ether, methyl t-butyl ether, methylene chloride, ethyl acetate, ethylene glycol, glycerin, dimethylsulfoxide, dimethylformamide, acetic acid, tetrahydrofuran (THF), and dioxane.

In aqueous solution at a pH of from 5.0 to 8.0, the loaded star polymers form dispersed particles having an average circular cross-sectional diameter of from 50 nm to 1500 nm, 50 nm to 1000 nm, 50 nm to 500 nm, 50 nm to 120 nm, as measured by dynamic light scattering. The loaded star polymers can comprise 0.1 to about 20 wt %, more particularly 5 to 20 wt %, and even more particularly 10 to 20 wt % of the cholesterol-lowering drug based on total dry weight of the loaded star polymer. The loaded star polymers can comprise 0.1 to about 20 wt %, more particularly 5 to 20 wt %, and even more particularly 10 to 20 wt % of the neutraceutical based on total dry weight of the loaded star polymer. A given dispersed particle can comprise one or more loaded star polymer macromolecules.

Optional Cargo Materials

The loaded star polymers can comprise both small molecular weight optional cargo materials in the size range from 100 daltons to about 1,000 daltons as well as larger macromolecular materials, such as peptide and protein drugs in the size range from about 1,000 daltons (Da) to about 100,000 daltons, and beyond.

Optional cargo materials include contrast enhancing agents, which have been considered for nuclear magnetic resonance imaging. These include soluble salts of paramagnetic metal ions, paramagnetic chelates and metallic complexes, and nitroxide stable free radicals. Paramagnetic metals ions include: from the transition metals series: titanium ($Ti^{3+}$), iron ($Fe^{3+}$), vanadium ($V^{4+}$), cobalt ($Co^{3+}$), chromium ($Cr^{3+}$), nickel ($Ni^{2+}$), manganese ($Mn^{2+}$), and copper ($Cu^{2+}$); from the Lanthanide series: praseodynium ($Pr^{3+}$), gadolinium ($Gd^{3+}$), europium ($Eu^{3+}$), and dysprosium ($Dy^{3+}$); from the Actinide series: protactinium ($Pa^{4+}$); and from nitroxide stable free radicals: pyrrolidine derivatives, and piperidine derivatives. Of these, the most favored contrast enhancing agents include complexes of ferric, chromium, and gadolinium ions, and stable nitroxide free radicals. Exemplary contrast enhancing agents for x-ray imaging include barium salts and halogenated materials, more particularly brominated and/or iodinated materials.

Organic contrast enhancing agents include porphyrinoids, which include but are not limited to porphyrins, corrins, chlorins, bacteriochlorophylls, phthalocyanines, tetraazaphyrins, texaphyrins, saphyrins, and the like. A nonlimiting example of a porphyrinoid compound is 5,10,15,20-(3,5-ditertbutylphenyl)porphyrin, where the ligand M can be a metal or two hydrogens (M=2H) (DTBP):

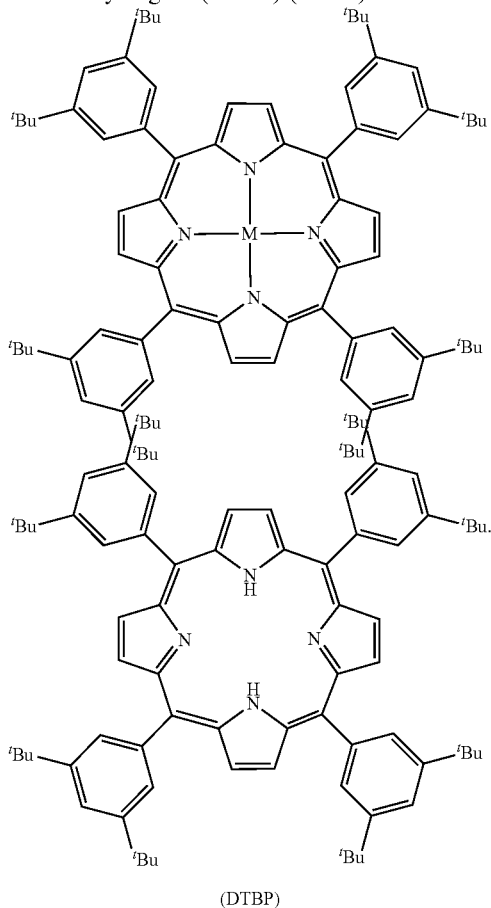

(DTBP)

Another non-limiting example of a porphyrinoid compound is tert-butyl phthalocyanine, wherein the ligand M can be a metal or two hydrogens (M=2H) (TBP):

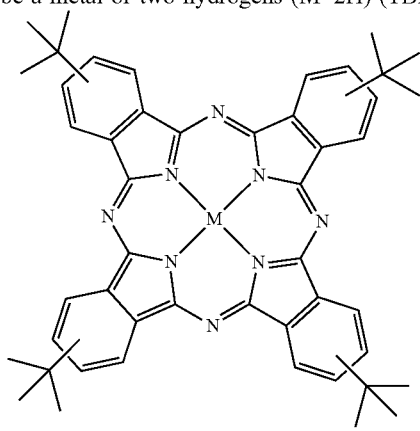

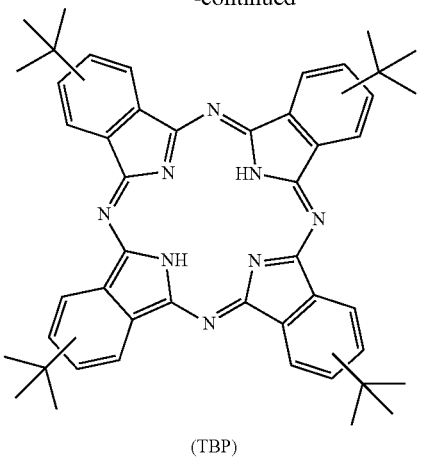

(TBP)

The contrast enhancing material can also comprise a combination of a porphyrinoid compounds. The porphyrinoid compound can further comprise a metal ligand that is a restricted metal.

The porphyrinoid compound can be in a non-aggregated state in the star polymer occlusion complex, detectable by the fluorescence of an aqueous mixture of the star polymer occlusion complex. In an embodiment, 10% to 100% by weight of the porphyrinoid compound in the star polymer occlusion complex is in a non-aggregated state. In another embodiment, 50% to 100% by weight of the porphyrinoid compound in the star polymer occlusion complex is in a non-aggregated state.

Other optional cargo materials include protein drugs, which include peptide hormones such as insulin, glucagon, parathyroid hormone, calcitonin, vasopressin, renin, prolactin, growth hormone; the gonadotropins including chorionic gonadotropin, follicle stimulating hormone, thyroid stimulating hormone and leutenizing hormone; physiologically active enzymes such as transferases, hydrolases, lyases, isomerases, phosphatases, glycosidases, superoxide dismutase, factor VIII, plasminogen activators; and other therapeutic agents including protein factors such as epidermal growth factor, insulin-like growth factor, tumour necrosis factor, transforming growth factors, fibroblast growth factors, platelet-derived growth factors, erythropoietin, colony stimulating factors, bone morphogenetic proteins, interleukins and interferons. Exemplary non-protein macromolecules include polysaccharides, nucleic acid polymers, and therapeutic secondary metabolites including plant products such as vinblastine, vincristine, taxol and the like.

Other optional cargo materials include commercially available drugs such as, for example, 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoin Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225, Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin Diftitox, DepoCyt™ Dexamethasone, Dexamethasone Acetate, Dexamethasone Sodium Phosphate Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™ Eloxatin™, Elspar®, Emcyt®, Epirubicin, Epoetin Alfa, Erbitux, Erlotinib, Erwinia L-asparaginase, Estramustine, Ethyol, Etopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, Gemzar, Gleevec™, Gliadel® Wafer, GM-CSF, Goserelin, Granulocyte-Colony Stimulating Factor, Granulocyte Macrophage Colony Stimulating Factor, Halotestin®, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan Idamycin®, Idarubicin, Ifex®, IFN-alpha Ifosfamide, IL-11 IL-2 Imatinib mesylate, Imidazole Carboxamide Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™, K Kidrolase (t), Lanacort®, Lapatinib, L-asparaginase, LCR, Lenalidomide, Letrozole, Leucovorin, Leukeran, Leukine™, Leuprolide, Leurocristine, Leustatin™ Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine Mutamycin®, Myleran®, Mylocel™, Mylotarg®, Navelbine®, Nelarabine, Neosar®, Neulasta™, Neumega®, Neupogen®, Nexavar®, Nilandron®, Nilutamide, Nipent®, Nitrogen Mustard, Novaldex®, Novantrone®, Octreotide, Octreotide acetate, Oncospar®, Oncovin®, Ontak®, Onxal™, Oprevelkin, Orapred®, Orasone®, Oxaliplatin, Paclitaxel, Paclitaxel Protein-bound, Pamidronate, Panitumumab, Panretin®, Paraplatin®, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, Raloxifene, Revlimid®, Rheumatrex®, Rituxan®, Rituximab, Roferon-A® (Interferon Alfa-2a) Rubex®, Rubidomycin hydrochloride, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, VP-16, Vumon®, Xeloda®, Zanosar®, Zevalin™, Zinecard®, Zoladex®, Zoledronic acid, Zolinza, and Zometa.

INDUSTRIAL APPLICATIONS

Further disclosed is a medical composition comprising a disclosed loaded star polymer and a second component, wherein the medical composition is suitable for treating a medical condition. The medical composition can be a liquid or a solid. In an embodiment, the second component is water. The medical composition can be administered by intravenous injection, by oral administration (e.g., liquid, pill), by inhalation spray, and/or combinations thereof. In another embodiment, the second component is a polymer binder (e.g., gelatin), which can serve, for example, to encapsulate the loaded star polymer and thereby provide a means for controlled release of the cargo material (e.g., release in the intestine rather than stomach). The encapsulated loaded star polymer can by administered by oral ingestion or as a suppository.

Further disclosed is a method of treating a cell, comprising contacting the cell with an above loaded star polymer, thereby changing the cell structure and/or activity.

No restriction is placed on the type of cell that can be treated with the loaded star polymers. In particular, the cells can be eukaryotic cells, mammalian cells, and more particularly human cells. The cells can be derived from various tissues, including extraembryonic or embryonic stem cells, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, dendritic cells, neurons, glia, mast cells, blood cells and leukocytes (e.g., erythrocytes, megakaryotes, lymphocytes, such as B, T and natural killer cells, macrophages, neutrophils, eosinophils, basophils, platelets, granulocytes), epithelial cells, keratinocytes, chondrocytes, osteoblasts, osteoclasts, hepatocytes, and cells of the endocrine or exocrine glands, as well as sensory cells.

The preparation and use of star polymers and loaded star polymers are further illustrated by the following examples.

EXAMPLES

Materials used in the following examples are listed in Table 8.

TABLE 8

| Abbreviation | Description | Source |
| --- | --- | --- |
| DMAEMA | 2-(N,N-Dimethylamino)Ethyl Methacrylate | Sigma Aldrich |
| CoQ10 | Ubiquinone, Coenzyme Q10 | Sigma Aldrich |
|  | Simvastatin | Sigma Aldrich |
| TBAF | Tetrabutylammonium Fluoride 3-Tert-Butyldimethylsilyloxy)-1-Propyl Lithium | Sigma Aldrich Gelest |

TABLE 8-continued

| Abbreviation | Description | Source |
|---|---|---|
| PMDETA | N,N,N',N'',N''-Pentamethyldiethylenetriamine | Sigma Aldrich |
| | Cyclohexane | Sigma Aldrich |
| Cu(I)Cl | Copper(I) Chloride | Sigma Aldrich |
| | P-Divinylbenzene | Sigma Aldrich |
| | 2-Bromoisobutyryl Bromide | Sigma Aldrich |
| | Triethylamine | Sigma Aldrich |
| EtOH | Ethanol | Sigma Aldrich |
| MeOH | Methanol | Sigma Aldrich |
| DCM | Dichloromethane | Sigma Aldrich |
| THF | Tetrahydrofuran | Sigma Aldrich |

Herein, Mn is the number average molecular weight, Mw is the weight average molecular weight, and MW is the molecular weight of one molecule. Rh is the hydrodynamic radius. DP is the degree of polymerization.

Instrumentation $^1$H NMR spectra were obtained on a Bruker Avance 2000 spectrometer (400 MHz) using 5 mm outside diameter tubes and were referenced to internal solvent residue ($^1$H, CDCl$_3$: delta=7.24). Analytical Gel Permeation Chromatography (GPC) using Waters high resolution columns HR1, HR2, HR4E and HR5E (flow rate 1 mL/minute, THF) was used to determine molecular weight distributions, Mw/Mn, of polymer samples with respect to linear polystyrene standards. Absorption studies were performed using a 8453 Agilent UV-VIS spectrophotometer.

Star Polymer

The star polymer architecture used in forming the occlusion complexes below has i) a crosslinked hydrophobic core, ii) about 34 independent arms covalently bound at one end to the hydrophobic core, wherein the arms comprise a) respective inner hydrophobic poly(styrene) blocks (3 kDa, DP=31) bound to a crosslinked poly(divinylbenzene) core (DP=170) and b) respective peripheral hydrophilic blocks (6 or 8 kDa, DP=21) comprising poly(2-(N,N-dimethylamino) ethyl methacrylate). The star polymers have a hydrodynamic radius of 8.8 nm. The cargo materials are coenzyme Q10 (nutraceutical) and a simvastatin (cholesterol-lowering drug). The poly(dimethylaminoethyl methacrylate) peripheral block provides both water solubility and additional adsorption sites for cargo materials.

Ubiquinone (coenzyme Q10, also referred to below as CoQ10), simvastatin, and tetrahydrofuran (THF, free of stabilizers) were obtained from Sigma-Aldrich and used as received.

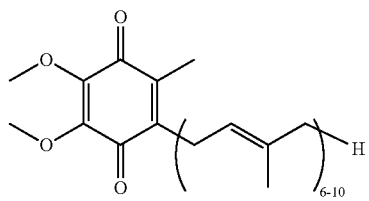

Ubiquinone (Coenzyme Q10)

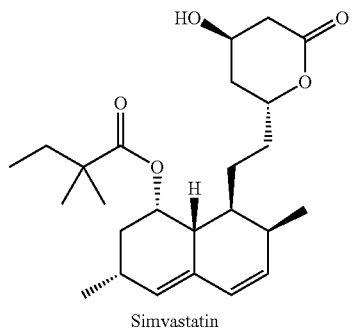

Simvastatin

The synthesis and characterization of nanogel core star polymers followed the procedure described by Lee V. Y., et al., "Nanogel Star Polymer Architectures: A Nanoparticle Platform for Modular Programmable Macromolecular Self-Assembly, Intercellular Transport, and Dual-Mode Cargo Delivery", J. Advanced Materials, 2011, volume 23, pages 4509-4515.

Preparation of Star Polymer SP-1

The preparation of SP-1 has four steps (A)-(D).

(A) Synthesis of Precursor 1 by anionic polymerization. Precursor 1 is a "protected" 3-(tert-butyldimethylsilyloxy)-1-propyl terminated polystyrene star polymer (Typical Procedure).

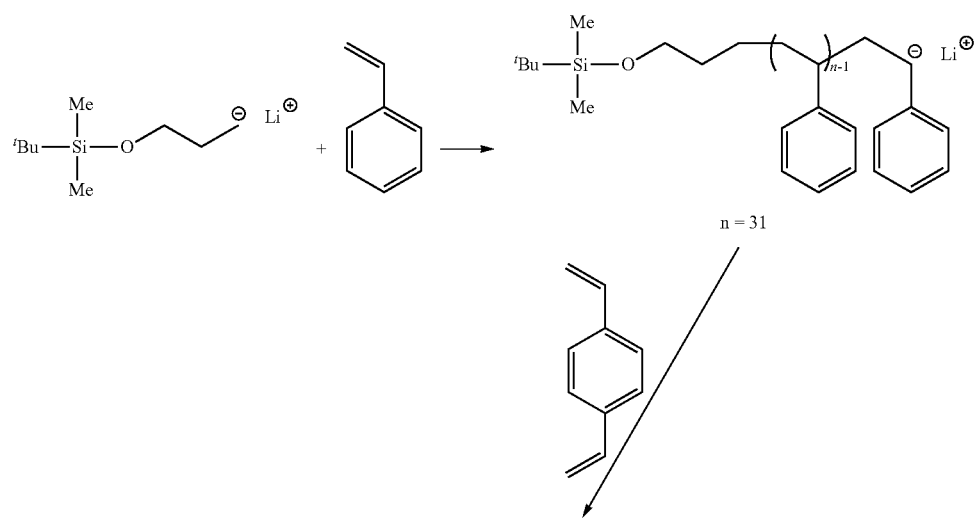

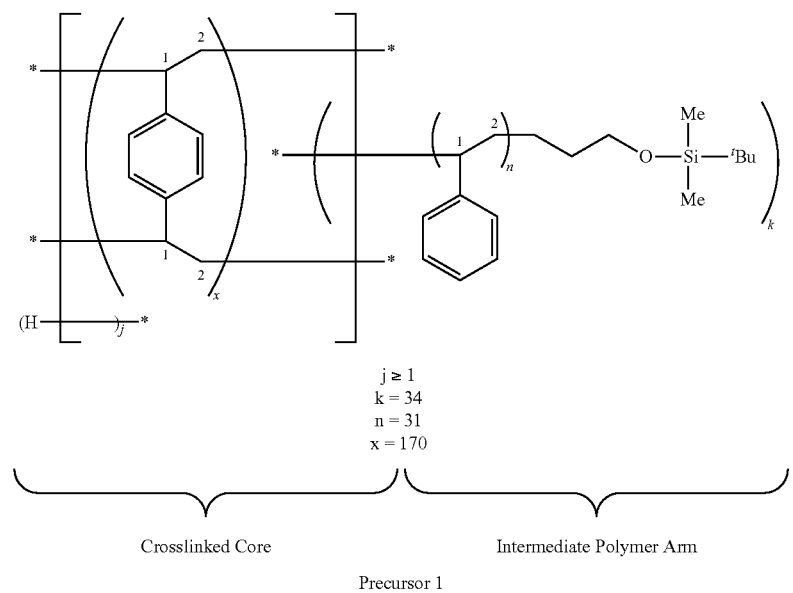

Precursor 1 j ≥ 1
k = 34
n = 31
x = 170

Crosslinked Core — Intermediate Polymer Arm 3-(t-Butyldimethylsilyloxy)-1-propyl lithium (15.5 mL, 20 wt % solution in cyclohexane) was added to a stirred solution of styrene (28.00 mL) in a cyclohexane (266 mL) and THF (14 mL) mixture under an argon atmosphere. After 20 minutes an aliquot (2 mL) was taken, quenched in degassed MeOH (150 mL) and a representative sample of the "free" polystyrene arm collected by filtration. A mixture of p-divinylbenzene (3.60 mL, 3.27 g, 25.2 mmol, density=0.914 g/mL, MW 130.19) in cyclohexane (3.60 mL) was added and the reaction mixture stirred for a further 40 minutes. The reaction solution was then quenched by slow addition to a rapidly stirred solution of methanol (MeOH) and ethanol (EtOH) (1.5 L, 1:1). The resulting precipitate was isolated by filtration and air dried to a constant weight. The crude star-polymer was then dissolved in dichloromethane (DCM) (100 mL) before the slow addition of acetone (150 mL) and then isopropyl alcohol (30 mL). The solution was allowed to stand until the product formed a substantial oily layer on the bottom of the container. The mixture was decanted allowing isolation of the oil which was then dried in a vacuum oven to constant weight affording the "protected" intermediate star polymer (Precursor 1, 16.5 g). $^1$H NMR (400 MHz, CDCl$_3$): delta 0.18 (br s, 6H), 0.73 (br s, 6H), 0.87 (br s, 9H), 1.45-2.24 (br m, 102 H), 3.35 (br s, 2 H), 6.52-7.10 (br m, 156 H). Analytical GPC: Mw/Mn=1.22. Light Scattering: Mw=106,000 g/mol, Mn=97,247, Mw/Mn=1.09, Rh(avg) 7.2 nm. $^1$H NMR (400 MHz, CDCl$_3$) analysis of the "free arm" sample indicated arm length of approximately 31 repeat units. This implied the approximate number of polymer arms of the star-polymer was about 34. $^1$H NMR analysis indicated there were 5 units of divinylbenzene per arm, therefore x=5×34=170 in the above structure of Precursor 1.

It should be understood from the above structure of Precursor 1 that the repeat units derived from styrene and divinylbenzene are randomly distributed in the crosslinked microgel core, indicated by vertical stacking of these repeat units within the square brackets. An atomic center within the square brackets having a bond to an asterisk overlapping a square bracket can be linked to any atomic center outside the square brackets that has a bond to an asterisk overlapping the same square bracket. Thus, carbon labeled 1 of the terminal styrene repeat unit of each of the k=34 polymer arms outside the right square bracket can be linked to any carbon labeled 2 of a divinylbenzene repeat unit within the square brackets. Additionally, each of the j≥1 chain terminating hydrogens of the microgel core can be linked to any carbon labeled 1 of a divinylbenzene repeat unit within the square brackets. The same considerations apply to the following structures.

(B) Synthesis of Precursor 2, a "deprotected" hydroxy-terminated polystyrene star polymer (Typical Procedure).

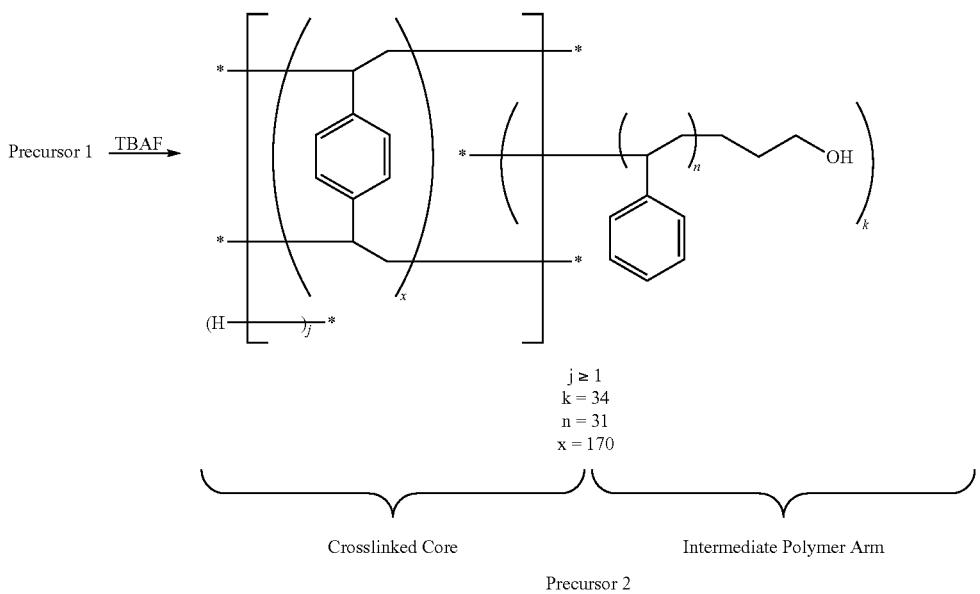

Precursor 2

Precursor 1 (10.0 g) was dissolved in THF (9.0 mL), and tetra-(n-butyl)ammonium fluoride (1.0 M solution in THF, 10.0 mL) was added. The reaction solution was stirred for 60 hours at room temperature before being warmed to 50° C. for 1 hour. The solution was allowed to cool to room temperature before it was slowly added to MeOH (1 L) with rapid stirring. The precipitate formed was isolated by filtration and air dried to a constant weight to afford the deprotected Precursor 2 (9.2 g). $^1$H NMR (400 MHz, CDCl$_3$), delta=1.45-2.24 (br m, 102 H), 3.45 (br s, 2 H), 6.52-7.10 (br m, 156 H). Analytical GPC: Mw/Mn=1.14. Light Scattering: Mw=106,000 g/mol, Mw/Mn=1.18, Rh(THF, average) 7.20 nm.

(C) Synthesis of Precursor 3, a polystyrene star polymer peripherally functionalized with atom transfer radical polymerization (ATRP)-initiator moiety.

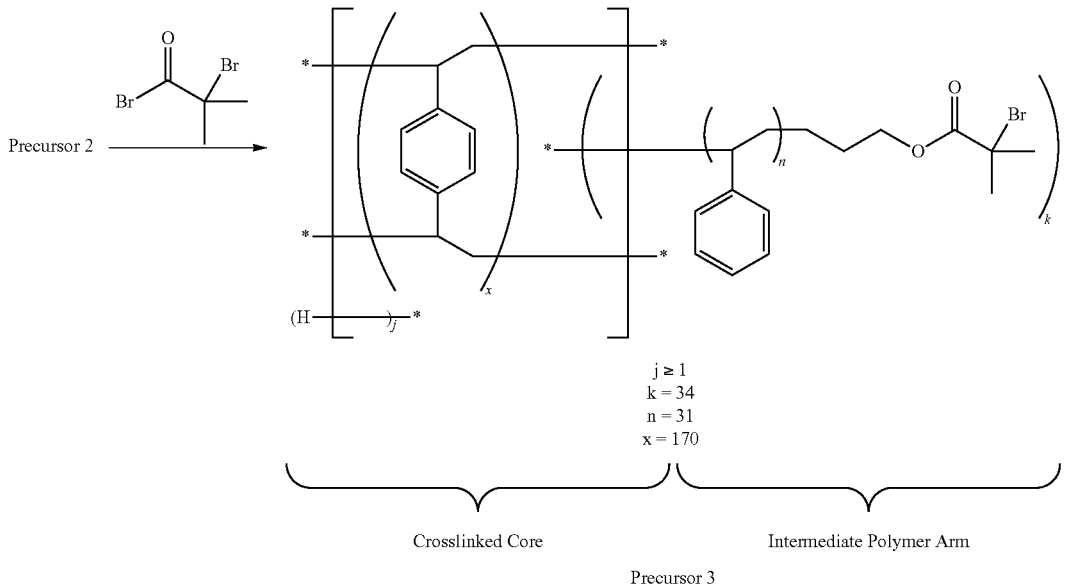

Precursor 3

A solution of 2-bromoisobutyryl bromide (1.4 g, 4 equivalents per star polymer alcohol end group) in anhydrous DCM (30 mL) was added dropwise over 15 minutes to a solution of hydroxy star polymer Precursor 2 (5.0 g) and triethylamine (0.75 g) in anhydrous DCM (30 mL) at 0° C. The mixture was allowed to warm up to room temperature for 14 hours, then heated to a gentle reflux for 4 hours. Pure product Precursor 3 was obtained after repeated precipitation into methanol. Gel permeation chromatography (GPC) and dynamic light scattering (DLS) analyses showed no significant change in molecular weight from that of the hydroxy star polymer starting material. $^1$H NMR (CDCl$_3$, 4000 MHz) characterization of the product confirmed quantitative end-group transformation.

(D) Synthesis of SP-1, a polystyrene star polymer terminated with poly(2-(N,N-dimethylamino)ethyl methacrylate) (DMAEMA)

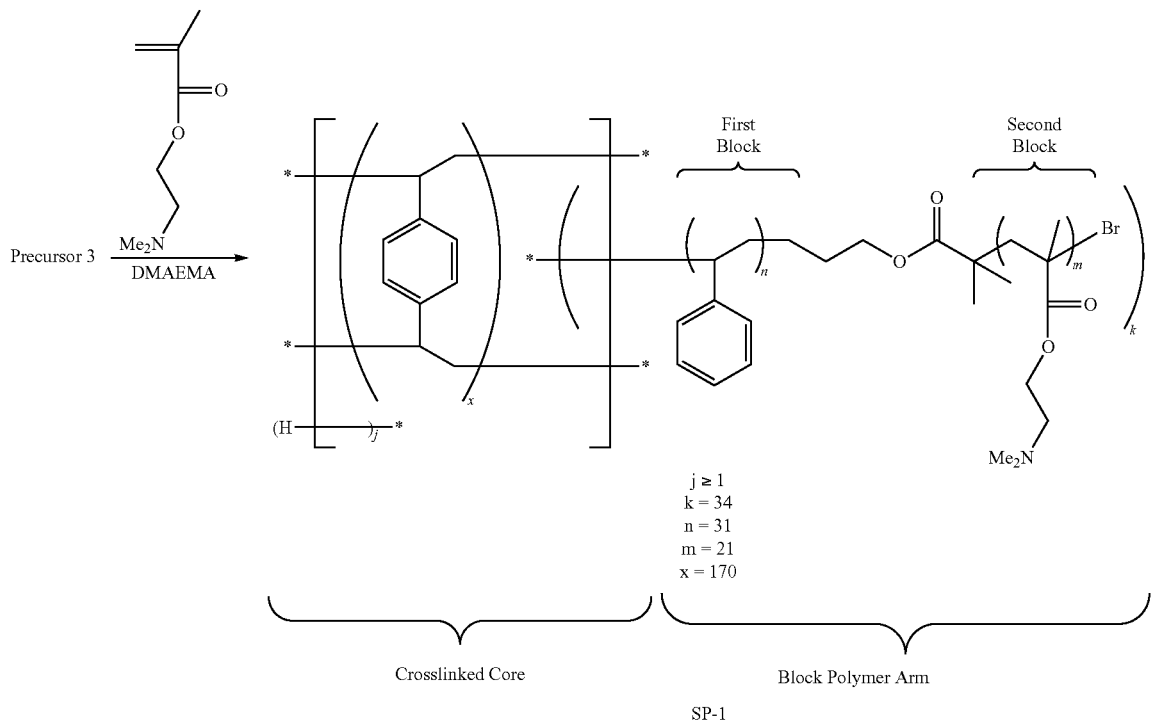

SP-1

ATRP-initiator peripherally functional polystyrene (PS) star polymer Precursor 3 (0.5 g), N,N-dimethylaminoethyl methacrylate (DMAEMA) (3.39 g), copper(I) chloride (Cu (I)Cl) (13.0 mg) and N, N, N',N'',N'-pentamethyldiethylenetriamine (PMDETA) (23.0 mg) were dissolved in anhydrous anisole (16.0 mL). The solution was degassed and sealed under a nitrogen atmosphere before being heated to 45° C. for 35 minutes. The reaction solution was then cooled and added to hexane (50 mL) with rapid stirring. The precipitate thus formed was isolated, dissolved in methylene chloride and again added to hexane (50 mL) with rapid stirring. The precipitate thus formed was isolated and air dried to a constant weight to produce star polymer SP-1 (0.35 g) as a white solid. $^1$H NMR (400 MHz, CDCl$_3$) delta (ppm)=0.78 (br, s, 6H), 0.90-1.08 (br s, 42 H), 1.45 (br s, 31 H), 1.86 (br s, 64 H), 2.32 (br s, 62 H), 2.63 (br s 42 H), 4.11 (br s, 42 H), 6.52-7.10 (br m, 156 H). DLS (THF): Mw=118,000 g/mol, Mw/Mn=1.1, hydrodynamic radius Rh(avg)=8.8 nm. $^1$H NMR (400 MHz, CDCl$_3$) analysis of the sample indicated approximately 21 repeat units of DMAEMA per arm (m=21).

Loading Star Polymers with Hydrophobic Cargos

Method 1—simultaneous encapsulation. Nanogel core star polymer SP-1 was loaded with simvastatin and CoQ10. A representative procedure was performed as follows: Star polymer SP-1 (20 mg), CoQ10 (4 mg, initial cargo loading=20 wt % based on weight of star polymer), and simvastatin (6 mg, initial cargo loading=30 wt % based on weight of star polymer) were dissolved in anhydrous THF (0.2 mL). To the resulting homogeneous solution water (4 mL) was rapidly added while stirring. The resulting solution was sparged with N$_2$ (approximately 3 hours) to remove organic solvent residue and then filtered through a 0.4 μm nylon filter. The obtained solution was analyzed by ultraviolet-visible (UV-Vis) spectrometry to determine weight percent drug loading (DL %) and encapsulation efficiency (EE %).

Method 2—stepwise encapsulation. Star Polymer SP-1 (20 mg) and one of the two cargos (simvastatin or CoQ10) were dissolved in anhydrous THF (0.1 mL). The mixture was stirred until fully dissolved. To the resulting solution the other cargo material (simvastatin or CoQ10) dissolved in anhydrous THF (0.1 mL) was added. To the resulting homogeneous solution water (4 mL) was rapidly added while stirring. The obtained mixture was sparged with N$_2$ approximately 3 hours to remove residual organic solvent and then filtered through a 0.4 μm nylon filter. The obtained solution was analyzed by UV-Vis spectrometry to determine weight percent drug loading (DL %) and encapsulation efficiency (EE %).

Loading Results

Example 1

The first trial run consisted of encapsulation of both cargo materials (simvastatin and CoQ10) simultaneously as described above. UV-Vis spectral analysis indicated encapsulation efficiencies of 87% for simvastatin and 66% for CoQ10 for initial cargo loadings of 30 wt % and 20 wt %, respectively (summarized below in Table 9), based on total weight of loaded SP-1.

Example 2

For the second trial run, a stepwise encapsulation protocol was followed as described above. Simvastatin was added to the solution of star polymer in THF first followed by the addition of CoQ10. The UV-Vis analysis indicated encapsulation efficiencies of 54% for simvastatin and 91% for CoQ10.

Example 3

For the third trial run, a stepwise encapsulation protocol was followed according to Example 2, reversing the addition order (CoQ10 followed by simvastatin). The result was noticeably improved encapsulation efficiencies: 99% for simvastatin and 91% for CoQ10.

Table 9 summarizes the results of Examples 1-3. The loaded weight of each drug was determined by UV-Vis spectrometry.

The encapsulation efficiency (EE %) was calculated as follows.

EE %=(loaded weight of cargo)/(initial weight of cargo)×100%

The percent drug loading (DL %) was calculated as follows.

DL %=(loaded weight of cargo)/(total weight of loaded star polymer)×100%

TABLE 9

| Example | Method | Loaded Simvastatin (mg) | Loaded CoQ10 (mg) | Simvastatin (DL %) | CoQ10 (DL %) | Simvastatin EE %[a] | CoQ10 EE %[b] |
|---|---|---|---|---|---|---|---|
| 1 | Simultaneous | 5.3 | 2.6 | 19.0 | 9.3 | 87 | 66 |
| 2[c] | Stepwise | 3.2 | 3.6 | 11.9 | 13.4 | 54 | 91 |
| 3[d] | Stepwise | 5.9 | 3.6 | 20.0 | 12.2 | 99 | 91 |

[a]Based on initial weight of simvastatin = 6 mg
[b]Based on initial weight of CoQ10 = 4 mg
[c]Simvastatin added first, CoQ10 second.
[d]CoQ10 added first, Simvastatin second.

Figure 2:
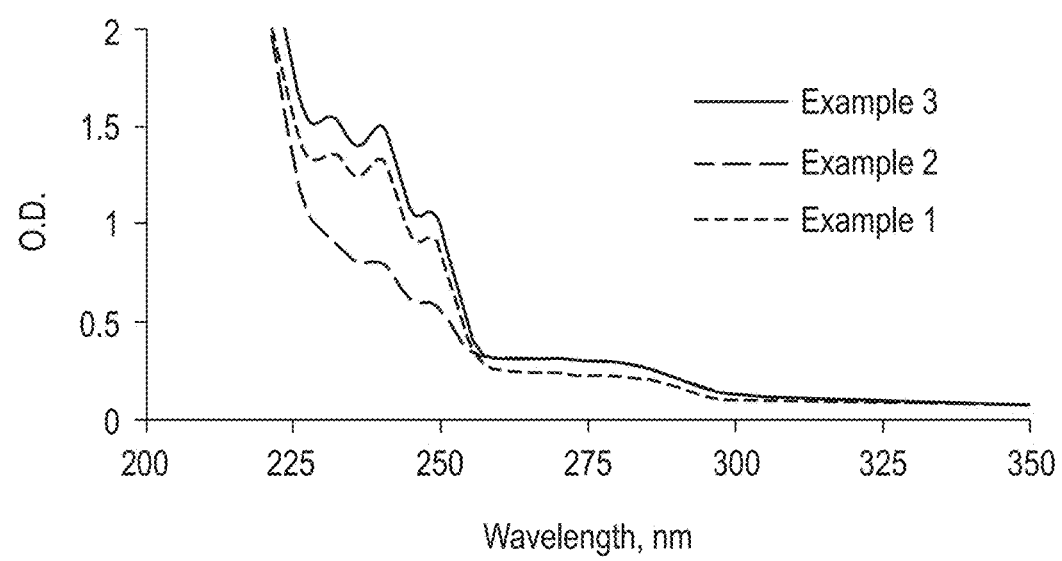
FIG. 2 is a graph showing the UV-Vis traces of the loaded star polymers of Examples 1-3.

FIG. 2 is a graph showing the UV-Vis traces of the loaded star polymers of Examples 1-3. Improved encapsulation efficiencies were observed by stepwise loading hydrophobic CoQ10 (log P ~21) followed by simvastatin. Without wishing to be bound by theory, the CoQ10 may act as a compatibilizer, making the core comparatively more hydrophobic and thereby more attractive to a hydrophobic simvastatin molecule.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. A loaded star polymer, comprising:
   a star polymer macromolecule, the star polymer comprising a crosslinked hydrophobic core covalently linked to a plurality of block polymer arms emanating from the core, wherein each arm comprises i) a hydrophobic first block linked to the core and ii) a peripheral second block linked to the first block, the second block comprising a repeat unit containing a sidechain tertiary amine group capable of undergoing protonation to form a hydrophilic tertiary ammonium ion;
   a cholesterol lowering drug selected from the group consisting of simvastatin, lovastatin, atorvastatin, fluvastatin, pitavastatin, pravastatin, and rosuvastatin, and combinations thereof; and
   a nutraceutical selected from the group consisting of ubiquinone (coenzyme Q10), menadione, duroquinone, idebenone, decylubiquinone, and combinations thereof; wherein
   the star polymer, the cholesterol lowering drug, and the nutraceutical are bound together by non-covalent interactions, and
   the loaded star polymer is water-dispersible.

2. The loaded star polymer of claim 1, wherein the loaded star polymer is capable of releasing the cholesterol lowering drug and the nutraceutical in water at pH 5-6.

3. The loaded star polymer of claim 1, wherein the cholesterol lowering drug is simvastatin.

4. The loaded star polymer of claim 1, wherein the nutraceutical is ubiquinone.

5. The loaded star polymer of claim 1, wherein the core comprises a random copolymer of styrene and divinylbenzene.

6. The loaded star polymer of claim 1, wherein the first block is polystyrene.

7. The loaded star polymer of claim 1, wherein the second block comprises a repeat unit of structure

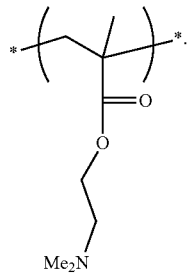

8. The loaded star polymer of claim 1, wherein the cholesterol lowering drug and the nutraceutical are in contact with the first block and/or the core of the star polymer.

9. The loaded star polymer of claim 1, wherein in water the loaded star polymer forms a particle having an average circular cross-sectional diameter between 0 and 500 nm.

10. The loaded star polymer of claim 1, wherein the loaded start polymer comprises about 10-20 wt % of the cholesterol lowering drug based on total weight of the particle.

11. The loaded star polymer of claim 1, wherein the loaded star polymer comprises about 9-12 wt % nutraceutical based on total weight of the particle.

12. The loaded star polymer of claim 1, wherein the star polymer macromolecule has an average radius of hydration (Rh) between 0 and 10 nm.

13. The loaded star polymer of claim 1, wherein the star polymer macromolecule has 30-40 block polymer arms.

14. A method of forming the loaded star polymer of claim 1, comprising:
   adding with agitation i) a first mixture comprising the nutraceutical and a first organic solvent to ii) a second mixture comprising the star polymer and a second organic solvent, thereby forming a third mixture;
   adding with agitation, to the third mixture, iii) a fourth mixture comprising the cholesterol-lowering drug and a third organic solvent, thereby forming a fifth mixture;
   adding with agitation water to the fifth mixture, thereby forming the loaded star polymer.

15. The method of claim 14, wherein the first solvent, second solvent, and the third solvent are the same.

16. A medical composition, comprising:
   the loaded star polymer of claim 1; and
   a second component in contact with the loaded star polymer.

17. The medical composition of claim 16, wherein the second component is a polymer binder.

18. The medical composition of claim 17, wherein the polymer binder is gelatin.

19. The medical composition of claim 16, wherein the medical composition is capable of being administered by oral ingestion.

20. The medical composition of claim 16, wherein the second component is water.

21. The medical composition of claim 20, wherein the medical composition is capable of being administered by injection.

* * * * *